(12) United States Patent (10) Patent No.: US 6,707,035 B2
Hughey et al. (45) Date of Patent: Mar. 16, 2004

(54) SAMPLE INTRODUCTION INTERFACE FOR ANALYTICAL PROCESSING OF A SAMPLE PLACED ON A SUBSTRATE

(75) Inventors: Barbara J. Hughey, Lexington, MA (US); Paul L. Skipper, Belmont, MA (US); John S. Wishnok, Brookline, MA (US); Ruth E. Shefer, Newton, MA (US); John T. Mehl, South Boston, MA (US); Steven R. Tannenbaum, Framingham, MA (US)

(73) Assignees: Newton Scientific, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/935,909

(22) Filed: Aug. 23, 2001

(65) Prior Publication Data

US 2002/0066857 A1 Jun. 6, 2002

Related U.S. Application Data

(63) Continuation-in-part of application No. 09/648,053, filed on Aug. 25, 2000
(60) Provisional application No. 60/227,711, filed on Aug. 24, 2000, and provisional application No. 60/227,839, filed on Aug. 25, 2000.

(51) Int. Cl.$^7$ .............................................. H01J 49/26
(52) U.S. Cl. .................. 250/288; 250/423 R; 250/282; 250/281; 250/423 P; 73/23.1
(58) Field of Search ............................ 250/288, 423 R, 250/282, 281, 423 P; 73/23.1

(56) References Cited

U.S. PATENT DOCUMENTS

| 5,209,919 | A |   | 5/1993 | Turtletaub et al. ........... 424/1.1 |
| 5,376,355 | A |   | 12/1994 | Turtletaub et al. ........... 424/1.1 |
| 5,438,194 | A | * | 8/1995 | Koudijs et al. ............. 250/288 |
| 5,959,297 | A | * | 9/1999 | Weinberg et al. ........... 250/288 |
| 6,451,616 | B1 | * | 9/2002 | Odom et al. ................ 436/173 |
| 6,455,844 | B1 | * | 9/2002 | Meyer ........................ 250/281 |

OTHER PUBLICATIONS

N.S. Belshaw et al. A SIMS method for $^{10}Be/^9Be$ ratio measurement in environmental materials. International Journal of Mass Spectrometry and Ion Processes 142 (1995) 55–67.

B.J. Hughey et al. Low–energy biomedical GC–AMS system for $^{14}C$ and $^3H$ detection. Nuclear Instruments and Methods in Physics Research B 172 (2000) 40–46.

Th.R. Niklaus et al. Progress report on the high–currention source of the Zürich AMS facility. Nuclear Instruments and Methods in Physics Research B 92 (1994) 96–99.

* cited by examiner

Primary Examiner—John R. Lee
Assistant Examiner—Zia R. Hashmi
(74) Attorney, Agent, or Firm—Samuels, Gauthier & Stevens LLP

(57) ABSTRACT

An interface system for introducing a non-gaseous sample as a predetermined gaseous form into an analytical instrument which comprises a substrate that receives the non-gaseous sample and a directed energy source that heats at least a portion of said substrate containing the non-gaseous sample to convert the sample to the predetermined gaseous form.

47 Claims, 16 Drawing Sheets

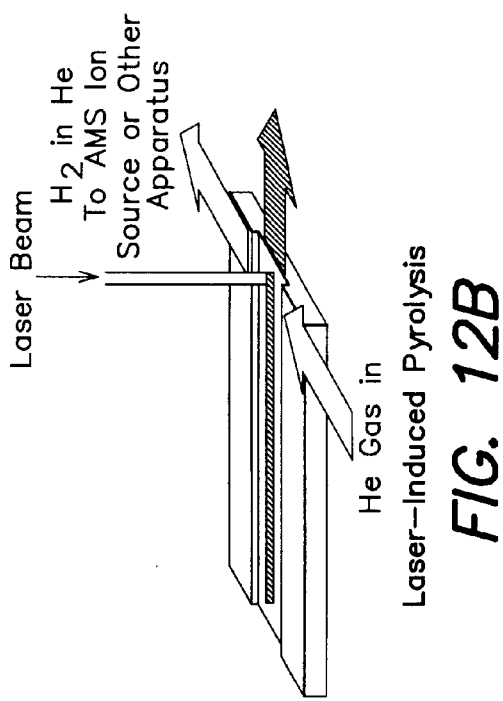
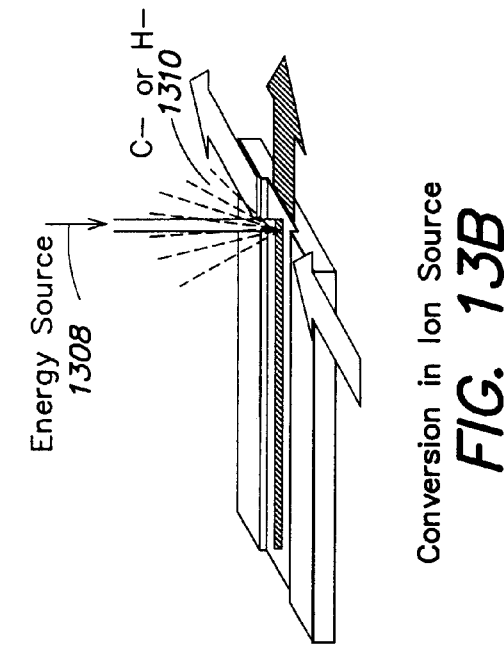
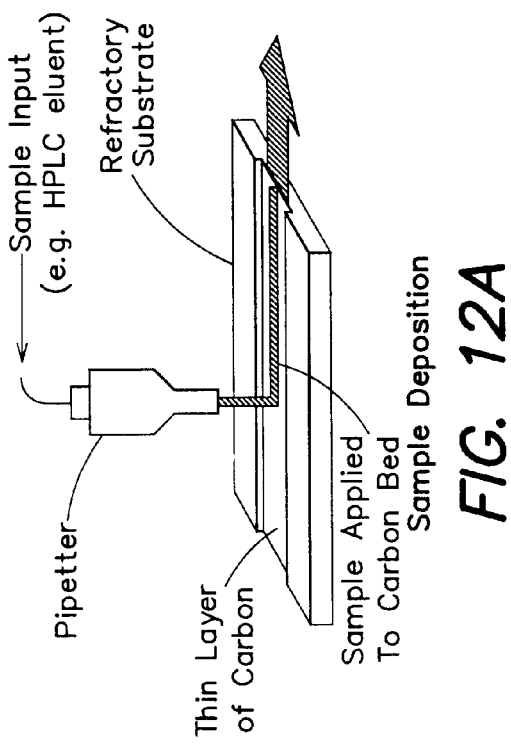
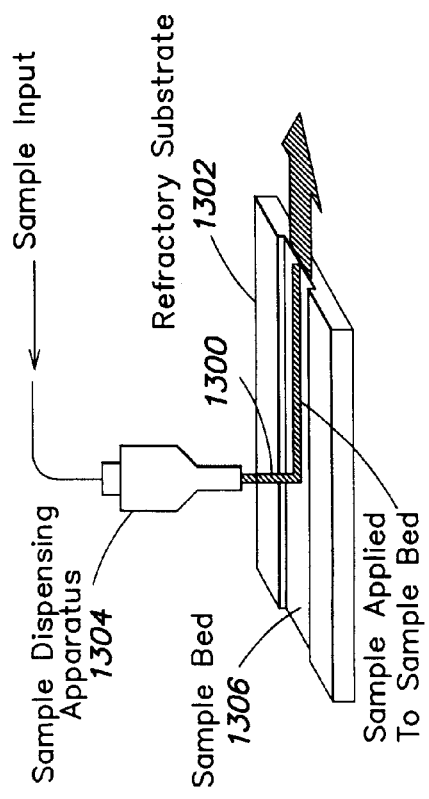
FIG. 12A — Sample Deposition
FIG. 12B — Laser-Induced Pyrolysis
FIG. 13A — Sample Deposition
FIG. 13B — Conversion in Ion Source

SAMPLE INTRODUCTION INTERFACE FOR ANALYTICAL PROCESSING OF A SAMPLE PLACED ON A SUBSTRATE

CROSS REFERENCE TO RELATED APPLICATIONS

This application is a continuation-in-part of co-pending application designated Ser. No. 09/648,053 filed Aug. 25, 2000 and entitled "Sample Introduction Interface for Accelerator Mass Spectrometry", and claims priority from the provisional application designated Ser. No. 60/227,711 filed Aug. 24, 2000 entitled "Sample Introduction Interface" and the provisional application designated Ser. No. 60/227,839 filed Aug. 25, 2000 entitled "Sample Introduction Interface". Each of these applications is hereby incorporated by reference.

This invention was made with government support under Grant No. CA66400, and CA76955 awarded by NIH and Grant No. DMI-9634259 awarded by NSF. The government has certain rights in the invention.

BACKGROUND OF THE INVENTION

The present invention relates to a method and apparatus for the introduction of selected chemical elements present in solid or liquid samples into an accelerator mass spectrometry (AMS) system or other analytical instrument.

AMS is a powerful tool for the ultra-sensitive detection of $^{14}C$ and $^{3}H$ in biological samples, with proven applicability to current problems in environmental toxicology and human carcinogenesis. For $^{14}C$ detection, AMS has 1000-fold higher sensitivity than liquid scintillation decay counting, thereby allowing the quantization of attomole ($10^{-18}$ mole), or smaller, samples. Almost all existing radiocarbon AMS systems require that the sample to be analyzed be introduced into the ion source as solid graphite. Graphitization is a lengthy process (typically taking 6–10 hours) and considerable skill is required to produce layers of uniform composition and thickness and to prevent sample contamination. For example see the paper by J. S. Vogel, K. W. Turteltaub, J. S. Felton, B. L. Gledhill, D. E. Nelson, J. R. Southon, I. D. Proctor and J. C. Davis Nucl. Instr. and Meth. B52 (1990) 524, incorporated herein by reference. Therefore, the analysis of biological samples by AMS requires highly specialized sample preparation procedures that are not compatible with standard chromatographs. This requirement has been a major impediment to the use of AMS in the biomedical sciences.

Liquid chromatography is the technique of choice for high performance separation of large, non-volatile or polar molecules such as proteins, carbohydrates, peptides, and oligonucleotides. The coupling of a liquid chromatograph (LC) to an AMS is particularly challenging because the interface must provide for the efficient conversion of biological molecules in a variety of solvents into $CO_2$ or $H_2$, and must do so with high sample transfer efficiency, good peak shape retention, and minimal contamination with naturally occurring $^{14}C$ or $^{3}H$ from other sources such as solvents and previous samples.

To prepare a liquid-phase sample for AMS, the interface must efficiently convert the desired isotope into one or more gaseous compounds suitable for introduction into the ion source. Negative ion sources that allow the sample to be introduced as gaseous $CO_2$ (or $H_2$) have been developed, and have been shown to have sufficiently low sample-to-sample memory for detection of $^{14}C$ at or near modern abundance. For example, see the paper by C. R. Bronk and R. E. M. Hedges, Nucl. Instr. Meth. Phys. Res. B29(1987) 45; also R. Middleton, J. Klein and D. Fink, Nucl. Instr. Meth. Phys. Res. B43 (1989) 231, incorporated herein by reference. In the ion source, $CO_2$ (or $H_2$) is converted to $C^-$ (or $H^-$) for injection into the accelerator mass spectrometer. The AMS ion source may produce positive ions as an intermediate step, as described in U.S. Pat. No. 5,438,194, entitled "Ultra-Sensitive Molecular Identifier", by Koudijs et al. A sample chromatogram is illustrated in FIG. 1. However, the applicability of GC-AMS is limited to volatile substances.

For some isotopes, such as $^{14}C$, it is important to strip a large fraction of the solvent accompanying the analyte. The extremely low naturally occurring background of tritium lowers the concentration at which samples can be introduced before separation of analyte from sample matrix (e.g., solvent) becomes necessary. The natural abundance of $^{3}H$ ($^{3}H:^{1}H$) is $\leq 10^{-15}$, at least 3 orders-of-magnitude lower than the natural abundance of $^{14}C$. The impact of the lower natural abundance of $^{3}H$ on AMS measurement capabilities can be seen from the following considerations. If it is assumed that the current produced by the AMS ion source is 25 μA, then the particle current of $H^-$ or $C^-$ is $10^{16}$ ions/min. For $^{3}H$ detection, a transport efficiency of 50% and a natural abundance of $10^{-15}$ yields a corresponding $^{3}H$ background of 5 cpm at the AMS detector. Detection of $^{3}H$ with SNR=10 in 1 minute would therefore require 105 cpm $^{3}H$ from analyte. In this example, the concentration of $^{3}H$-labeled analyte is 2.2 pM (105 cpm $^{3}H \div 0.5 \times 10^{16}$ cpm H, multiplied by 100 moles H/L) and the volumetric flow rate of sample introduced into the ion source is about 1 nL/min. It is clear from these numbers that, even at these very low sample concentrations and flow rates, accurate AMS detection of $^{3}H$ without solvent removal is possible with negligible contribution from naturally occurring background.

The limits on direct sample introduction for $^{14}C$ detection are more difficult to define, but are clearly more stringent. For $^{14}C$, the natural abundance of $1.4 \times 10^{-12}$ gives a background count rate of 6,600 cpm under the same assumptions used above. Detection of the same number of $^{14}C$ atoms from analyte (105 cpm) yields a SNR=1.3. In order to obtain the same statistical accuracy of SNR=10, it would be necessary remove solvent to a level of about one part in $10^3$ prior to AMS analysis. Alternately, higher flow rates of sample into the AMS could be used. In this example, about 900 cpm $^{14}C$ from analyte (in a background of 6,600 cpm from solvent) would yield a SNR=10 due to counting statistics alone, but it would be necessary to eliminate all other noise contributions at the level of better than 1.5%. For these reasons, accurate $^{14}C$ detection by AMS without solvent removal is extremely difficult.

U.S. Pat. No. 5,438,194, entitled "Ultra-Sensitive Molecular Identifier", by Koudijs et al. discloses a system where a liquid or gas chromatograph is coupled directly to the ion source system of an AMS analyzer. However, there are no provisions for desolvation, and the molecular dissociation and ion formation occur in the same process in the ion source itself. In addition, the inventors disclose several designs for the ion source system. However, none of these disclosed designs include a provision for desolvation. At a relatively low solvent flow rate of 1 μL/min, the detection limit for $^{14}C$ without desolvation will be approximately 0.1 femtomole or higher. This is significantly greater than the target sensitivity for a LC-AMS system of detection of LC peaks containing one attomole ($10^{-3}$ femtomole), or less, of $^{14}C$ or $^{3}H$.

An additional disadvantage of the direct coupling of a liquid chromatograph to the ion source systems described in U.S. Pat. No. 5,438,194 is that molecular dissociation and ion formation (positive or negative) occur in the same process. This coupling of the dissociation and ionization functions will most likely result in a significant dependence of conversion efficiency on input chemical form. The prior art mentions the possibility of dissociating the molecules by high temperature pyrolysis, but there is no detailed description of what compounds are to be formed and whether the dissociation and ionization functions will be separated in this case.

Systems coupling a liquid chromatograph through a conversion reactor to a standard mass spectrometer have been developed for IRMS. These systems include the "moving wire" system as described by R. J. Caini and J. T. Brenna, Anal, Chem. 65 (1993) 3497, and the chemical reaction interface mass spectrometry (CRIMS) interface, as disclosed by M. McLean, M. L. Vestal, Y. Teffera, and F. P. Abramson, J. Chrom. A, 732 (1996), 189. The "moving wire" system has the disadvantage that only a small fraction of the LC eluent can be deposited on the wire, resulting in low analyte transfer efficiency to the IRMS. The CRIMS interface incorporates a Vestec "Universal Interface" (UI) to separate analyte from solvent. The UI is based on the formation of a highly focused particle beam using thermospray vaporization followed by a multiple-stage desolvation process (momentum separator). The UI operates at normal-bore HPLC flow-rates and uses a high He gas flow to carry the particle beam through the apparatus. The disadvantage of the particle beam desolvation approach for AMS is that existing technology is not scalable to the lower liquid flow rates (<1 $\mu$L/min) required for the analysis of extremely small samples.

The recent development of microscale analytical systems is relevant to the development of AMS as a biomedical assay technique. AMS systems, because of their extremely high sensitivity, are uniquely suited to analyze samples introduced using microfluidic devices. Using technology already highly developed in the electronics industry, many university researchers and commercial concerns are producing "lab-on-a-chip" chemical synthesis and analysis systems that reside on centimeter-sized wafers of silicon, glass, quartz, and polymers. For example, see the paper by R. F. Service, entitled "Labs on a chip: Coming soon: "The pocket DNA sequencer", Science 282 (1998) 399; and the paper by M. Freemantle, entitled "Downsizing chemistry", Chemical and Engineering News 77 (1999) 27, both incorporated herein by reference. These systems operate on nanoliter and smaller volume samples and thereby achieve dramatic improvements in sample throughput and speed of analysis while at the same time reducing costs by orders of magnitude.

Matrix-assisted laser desorption/ionization (MALDI) is another commonly used technique in mass spectrometry to desorb and ionize large molecules. In the MALDI technique, the sample is imbedded in a solid matrix, typically organic acid. The analytes are subsequently vaporized and ionized by pulsed laser irradiation, with the goal of retaining the analyte molecular form. This differs from the goal of the present invention, which is to convert selected chemical elements present in the analyte to a common form. A potential disadvantage of MALDI as the initial step of the present invention is the production of background organic molecules from the matrix that may limit the sensitivity achievable with the AMS. Techniques for matrix-free laser desorption using porous silicon as the substrate material have recently been developed that may have advantages over MALDI for AMS applications. For example, see the paper by J. Wei, J. M. Buriak, and G. Siuzdak, Desorption-ionization mass spectrometry on porous silicon. Nature 399 (1999), 243, incorporated herein by reference. Development of on-line LC/MALDI systems is ongoing in research laboratories around the world. Such a system may provide an alternative to electrospray for nebulizing and ionizing large molecules, but does not perform the required conversion of selected chemical elements into the gaseous compounds suitable for introduction into an AMS or other analytical instrument.

Therefore, there is a need for a system and method for converting a non-gaseous sample to a desired gaseous form for analytical processing (e.g., by an AMS), thus allowing standard liquid- and solid phase chemical separation techniques to be utilized to their full potential.

SUMMARY OF THE INVENTION

Briefly according to an aspect of the present invention, an interface introduces a solid or liquid sample into an AMS system or other analytical instrument. A non-gaseous sample is introduced into a converter stage, with provisions for separating the analyte molecules from accompanying matrix material (e.g., solvent, organic acid, etc.) if necessary. The converter converts the labeled molecules contained in the sample to one or more standard molecular forms (e.g., $CO_2$, $H_2$, etc.) for introduction into the AMS ion source chamber. The converter stage may be contained within the AMS ion source chamber, or separate from the AMS ion source chamber.

In one class of embodiments of the present invention, a first stage transfers analyte from a solid or liquid form into a stream of carrier gas, with provisions for separating the analyte molecules from accompanying matrix material (e.g., solvent, organic acid, etc.) if necessary. This step is referred to as nebulization for liquid samples, and desorption for solid samples. Alternatively, if it is known that separation of analyte from accompanying matrix material is not required, a liquid sample can be directly injected into the converter using a pipetter, obviating the need for the nebulization step. A second stage converts the labeled molecules contained in the sample to one or more standard molecular forms (e.g., $CO_2$, $H_2$, etc.) for introduction into the AMS ion source chamber.

According to one embodiment of the present invention, a sample is nebulized using electrospray and desired elements in the sample are converted to a predetermined gaseous form, which is input to an AMS system for analysis.

According to a second class of embodiments of the present invention, a sample is deposited onto a solid substrate, and desired elements of the sample are converted to a predetermined gaseous form, which is then provided to an analytical processing device for analysis. There are two general embodiments of this aspect of the invention. In a first embodiment a reaction chamber is connected to an AMS or other apparatus in such a manner as to permit the flow of gases from the one to the other and whose function is to convert the desired elements present in the sample into a gaseous form suitable for introduction into the AMS ion source or other apparatus. Samples to be analyzed are deposited onto or mixed with a solid support that may also be chemically reactive, and placed within the reaction chamber. Chemical conversion is accomplished by specifically directing heat or other forms of energy to the sample or to the substrate where the sample has been applied. If the substrate is itself not reactive, then a reactant gas may be introduced to the reaction chamber during the step of directly heating or applying other forms of energy to the sample or substrate. The application of energy to the sample region serves both to convert the desired elements in the sample to a predetermined chemical form and to release the product chemical from the substrate. A flow of gas passing through the reaction chamber carries the analyte elements in the predetermined chemical form into the AMS ion source.

In a second embodiment, sample is placed on a substrate that is introduced directly into the AMS ion source. The ion source converts the desired elements present in the analyte into ionic species suitable for extraction and injection into the AMS system. Conversion may take place via bombardment with a cesium beam, as in a cesium sputter ion source, or by any other interaction of constituents of the ion source with the sample and substrate.

In both embodiments of this second class of the invention, if analytes are present in solution, solvent may be removed by evaporation in the process of sample application to the requisite substrate. Both embodiments provide data in the form of isotope concentration as a function of position on the substrate. With appropriate knowledge of how samples were applied to the substrate, such data can be transformed to recreate a prior relationship between samples, as for example, the temporal or volumetric relationship between different components in the eluent of a chromatograph.

Depending on which input technology is selected, measurements are performed in one of two regimes of operation: (i) high resolution, or (ii) high throughput. Coupling the AMS system to a liquid chromatograph, capillary electrophoresis (CE), or other liquid-phase sample separation technique results in high-resolution measurements. Reconfiguration of the interface to couple small volume, microfluidic devices, or to introduce samples by laser induced desorption results in a high throughput analytical system. The second class of embodiments wherein sample is applied to a solid substrate have the advantage that they can be used both in the high resolution and in the high throughput mode.

Several embodiments of the present invention that are examples of these different regimes of operation include: (1) coupling of an LC to an AMS system with desolvation, for the analysis of $^{14}$C-labeled samples, (2) coupling of an LC to an AMS system without desolvation, for the analysis of $^3$H-labeled samples, (3) coupling a microfluidic device to the AMS system, (4) using laser induced desorption as the initial step in preparing samples for analysis by AMS, and (5) using laser-induced conversion to analyze either an LC chromatogram or a discrete (unfractionated) sample. Although the specific examples presented involve the detection of $^{14}$C or $^3$H, the technique applies to the detection of any low abundance isotope detectable by AMS, or the detection of other isotopes by other analytical techniques, such as IRMS.

These and other objects, features and advantages of the present invention will become apparent in light of the following detailed description of preferred embodiments thereof, as illustrated in the accompanying drawings.

BRIEF DESCRIPTION OF THE DRAWINGS

FIGS. 12A–12B illustrate the laser-induced sample conversion method for conversion of hydrogen-containing samples to $H_2$ for AMS analysis or other applications;

FIGS. 13A–13B illustrate yet another embodiment for the conversion of sample in an AMS ion source.

DETAILED DESCRIPTION OF THE INVENTION

Figure 1:
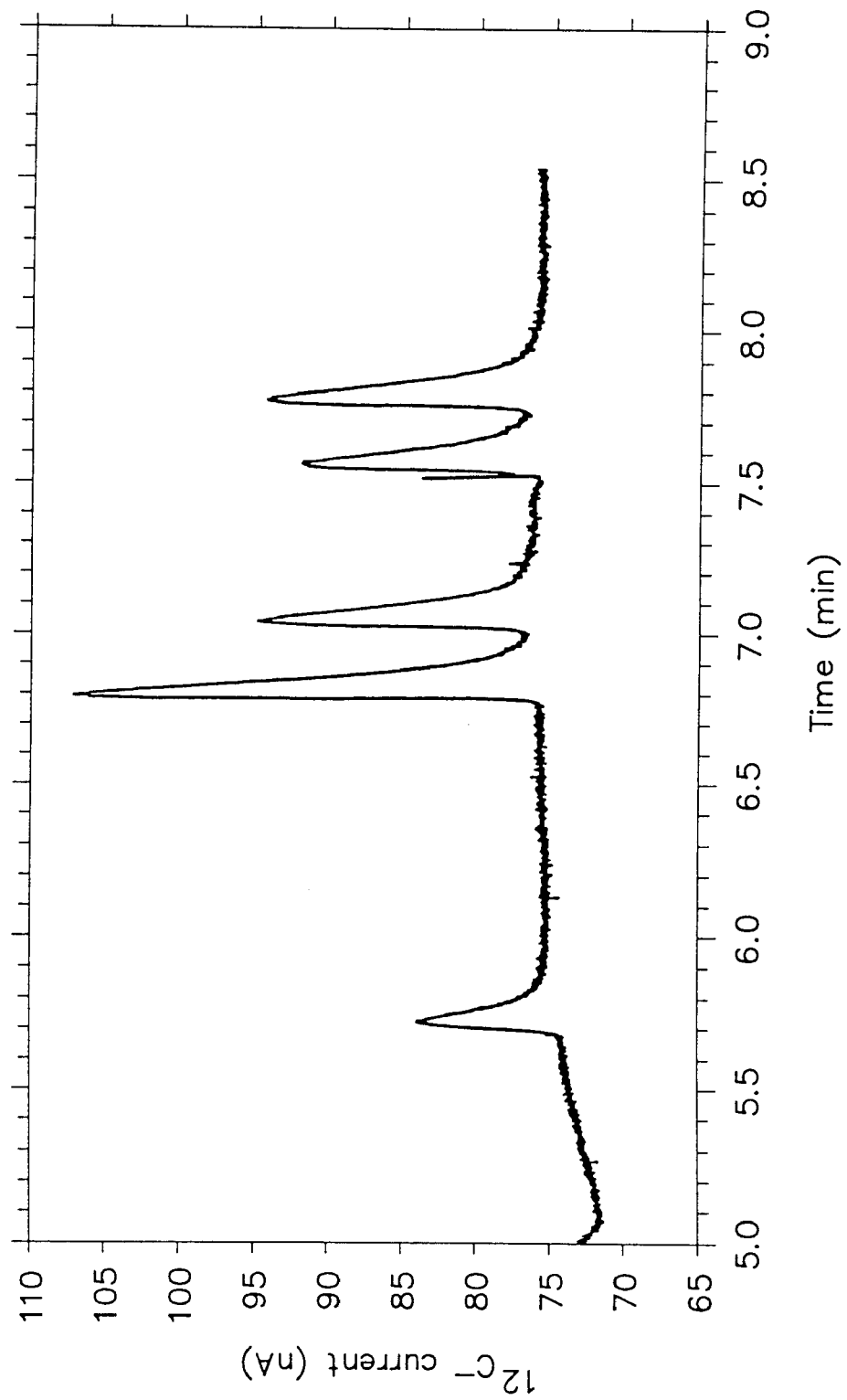
FIG. 1 illustrates a sample GC chromatogram.

FIG. 1 displays detection of an equimolar carbon standard with the AMS ion source. A mixture containing six compounds was injected into a GC-AMS interface, comprising a HP5890 gas chromatograph, CuO reactor to convert carbon to $CO_2$, Nafion dryer to remove $H_2O$ byproduct, and gas-fed Cs-sputter AMS ion source for conversion of $CO_2$ to $C^-$, which is detected in a Faraday cup. Compounds in order of elution time are: acetanilide, diethylphthalate and 4-chlorodiphenyl ether (unresolved), benzophenone, 9-fluorenone, and phananthrene.

Figure 2:
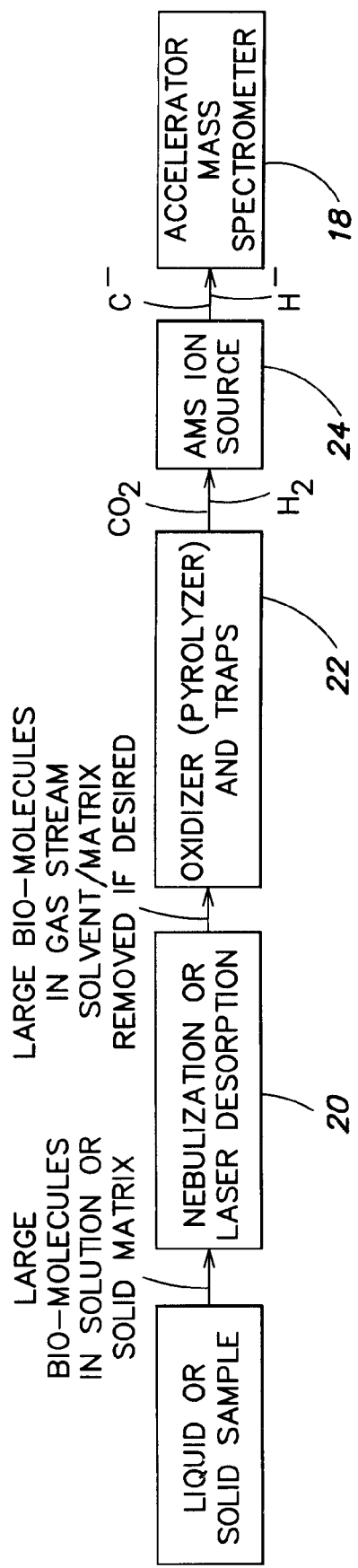
FIG. 2 is a functional illustration of an aspect of the present invention.

FIG. 2 is a functional illustration of an aspect of the present invention, which provides an interface for introducing solid or liquid samples (e.g., eluent from an LC or CE, or unfractionated biological material such as blood, urine, or tissue homogenate) into an accelerator mass spectrometer (AMS) system 18. A first stage 20 transfers analyte from a solid or liquid form into a stream of carrier gas, with provisions for separating the analyte molecules from accompanying matrix material (e.g., solvent, organic acid, etc.) if necessary. This step is referred to as nebulization for liquid samples, and desorption for solid samples. A second stage 22 converts the labeled molecules contained in the sample to one or more standard molecular forms (i.e., $CO_2$, $H_2$, etc.) for introduction into an AMS ion source chamber 24.

Five embodiments of the present invention are described as examples of these different regimes of operation: (1) coupling of an LC to an AMS system with desolvation, for the analysis of $^{14}$C-labeled samples, (2) coupling of an LC to an AMS system without desolvation, for the analysis of $^3$H-labeled samples, (3) coupling a microfluidic device to the AMS system, (4) using laser induced desorption as the initial step in preparing samples for analysis by AMS, and (5) using laser induced conversion to analyze either LC chromatogram or discrete (unfractional) sample. Although the specific examples presented involve the detection of $^{14}$C or $^{3}$H, the technique applies to the detection of any low abundance isotope detectable by AMS.

Figure 3:
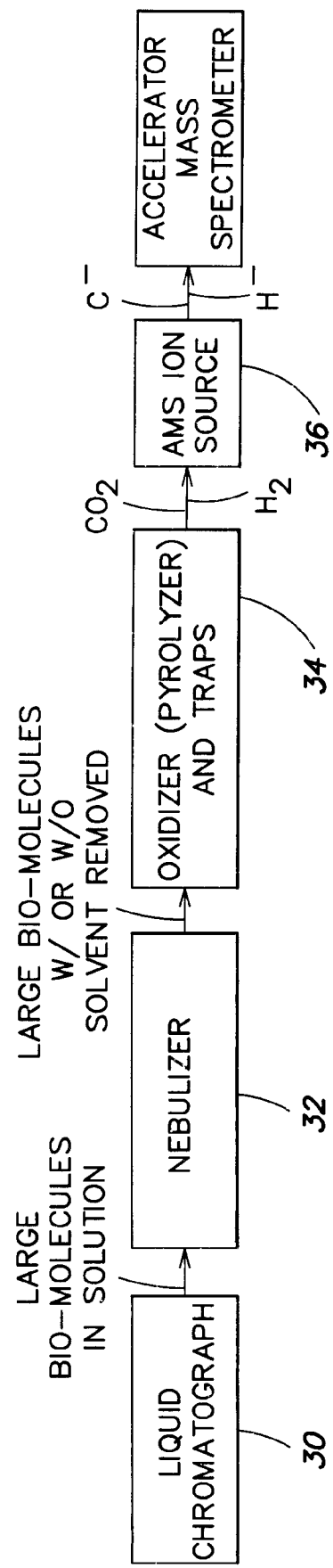
FIG. 3 is a functional illustration of two embodiments of the present invention.

FIG. 3 is a functional illustration of the first two embodiments of the present invention. Eluent from a liquid chromoatograph (LC) 30 (or CE, or other liquid-phase sample introduction system) enters a nebulizer 32 where analytes are separated from the mobile phase. Separation can be partial, and in some cases (such as for example tritium detection) this nebulizing step may be omitted. The nebulizer 32 is preferably based on electrospray technology, including micro-electrospray and nanospray, since this technology is well suited to handling small sample sizes and low flow rates (e.g., in the μL/min range and lower) and is compatible with CE as well as LC. Electrospray nebulization is described in the book "Electrospray Ionization Mass Spectrometry", ed. by Richard B. Cole (John Wiley and Sons, New York, 1997), incorporated herein by reference. An advantage of electrospray technology for AMS applications is that the ionization efficiency for electrospray increases as flow rate decreases. Desolvated analyte molecules emerging from the nebulizer 32 are directed into a reactor 34 in a stream of carrier gas that also serves to carry the product compounds into an ion source 36. It is contemplated that any reactor (e.g., catalytic oxidizer, high-temperature pyrolyzer, chemical, plasma, etc) that converts the sample isotope to the desired chemical form(s) can be used. For example, an oxidizer can be used to generate $CO_2$ as well as oxides of other atomic species, such as sulfur and nitrogen, for analysis. For nitrogen analysis, a reduction reactor to yield $N_2$ typically follows the oxidizing reactor. A high temperature reactor, or pyrolyzer, can be used to convert hydrogen in organic compounds to $H_2$.

Figure 4A:
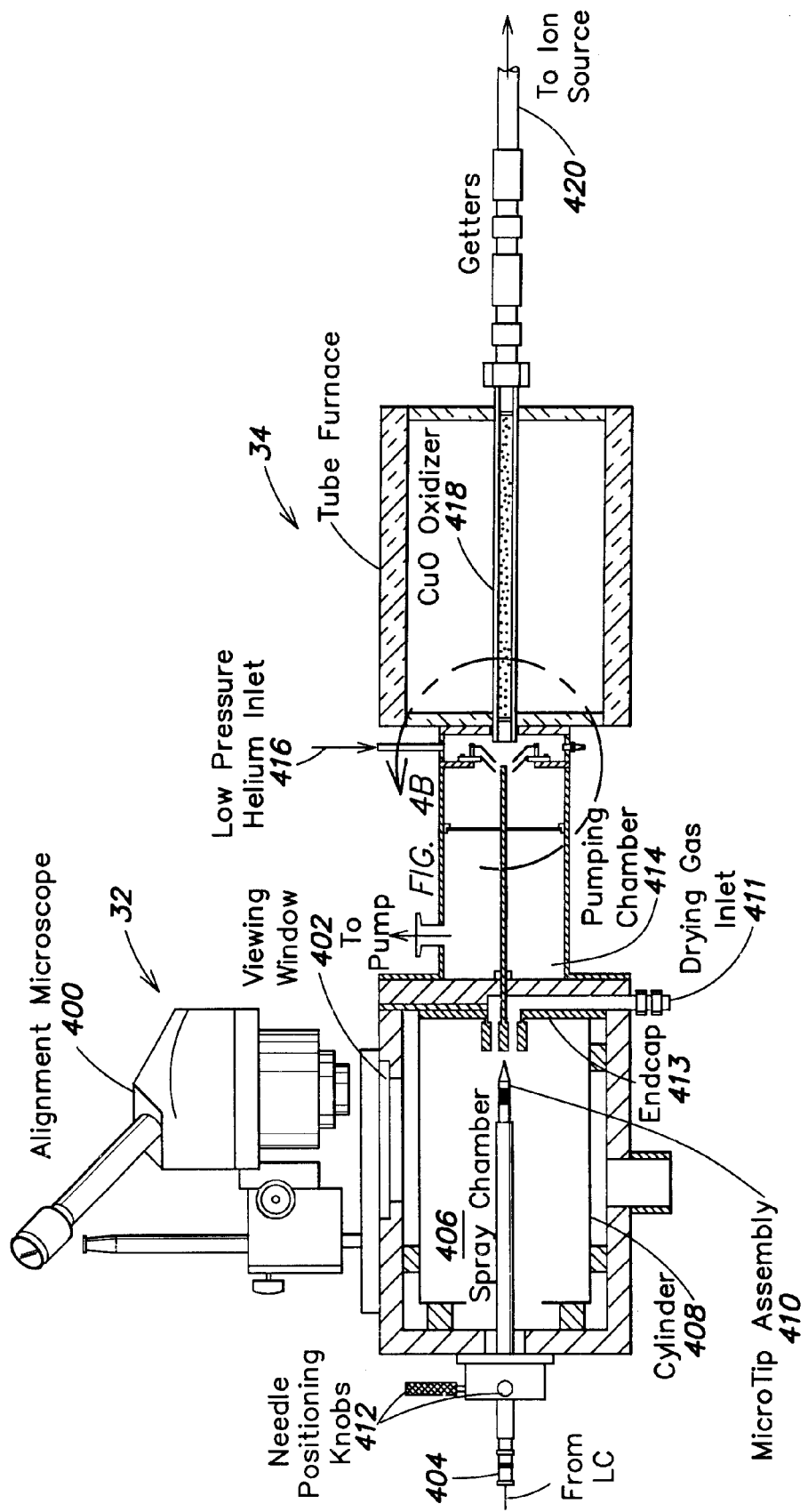
FIG. 4A is cross sectional illustration of a nebulizer and a reactor/CuO furnace, which converts sample carbon to $CO_2$.

FIG. 4A is cross sectional illustration of the nebulizer 32 and the reactor/CuO furnace 34, which converts sample carbon to $CO_2$. This type of reactor provides quantitative conversion (i.e., essentially 100% conversion) of sample carbon to $CO_2$ for organic compounds analyzed by GC-IRMS. For example see the paper by D. A. Merritt, K. H. Freeman, M. P. Ricci, S. A. Studley, and J. M. Hayes, Anal. Chem. 67 (1995), 2461; D. E. Mathews, J. M. Hayes, Anal. Chem. 50 (1978), 1465, incorporated herein by reference. If quantitative conversion can be maintained for the liquid phase input described herein, separation of the dissociation process from the ionization process by supplying the source with a constant chemical species (i.e., $CO_2$) should result in a yield of negative ions which is essentially independent of chemical form of input compound. Referring to FIG. 4A, the nebulizer 32 includes an alignment microscope 400 that is positioned over a viewing window 402. The nebulizer 32 is coupled to an LC via flow line 404 to introduce the sample to the nebulizer 32. The nebulizer includes a spray chamber 406 (e.g., at a pressure of about 760 torr) and a cylinder 408 at a potential of about 0.8–2.8 kv. A microtip assembly 410 within the chamber 406 is coupled to the sample flow line 404. Needle positioning knobs 412 are used to properly align the microtip assembly 410. The nebulizer also includes a drying gas inlet 411 and an endcap 413 at a potential of about 0.8–2.8 kv.

Figure 4B:
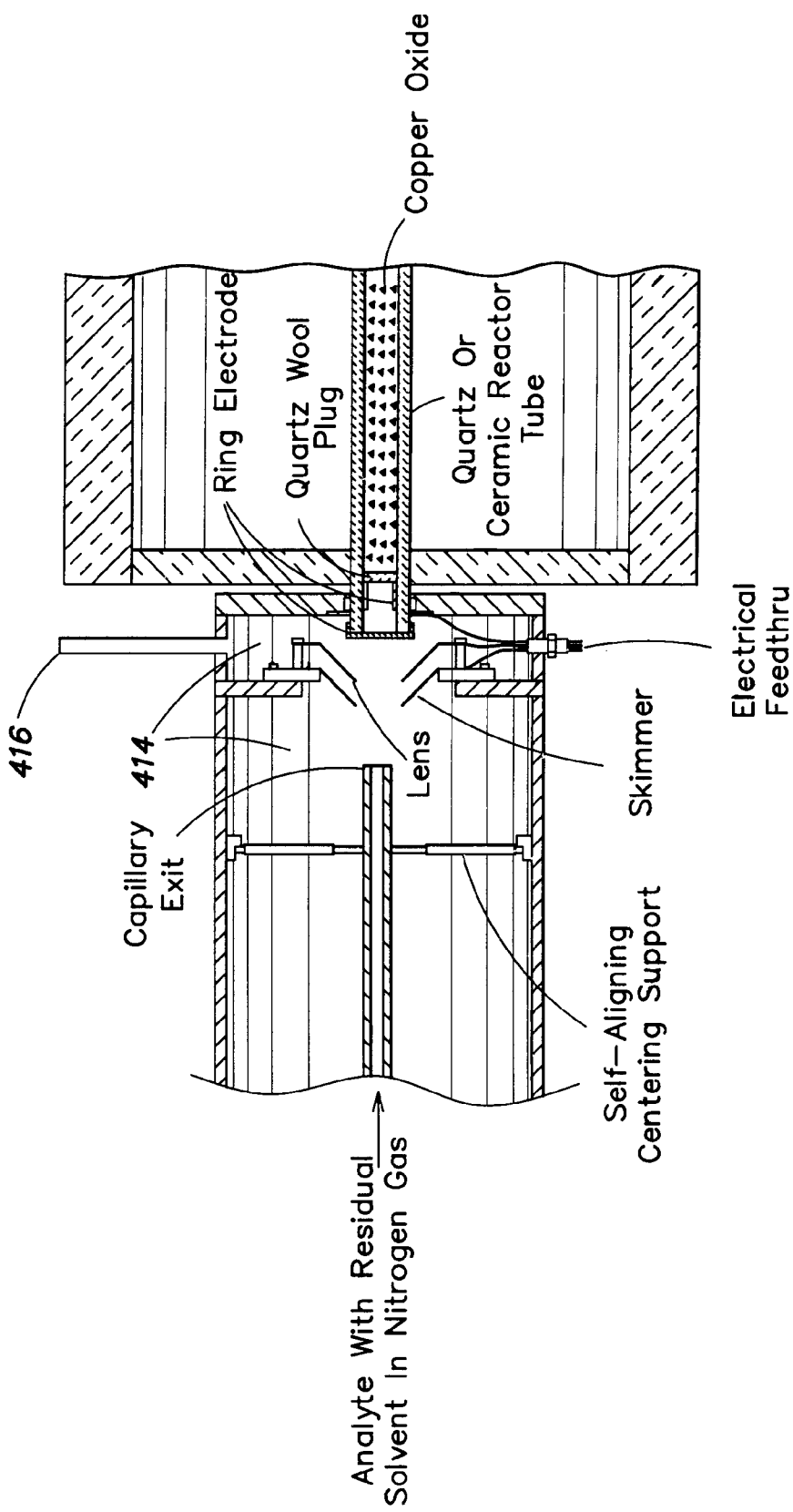
FIG. 4B illustrates an expanded view of the transfer capillary exit and the oxidizing reactor entrance.

A pumping chamber 414 couples the nebulizer 32 to the oxidizer 34. The chamber 414 is maintained at a pressure of about 1–5 torr by a pump (not shown) and includes a low pressure helium inlet 416. The oxidizer 34 preferably includes a CuO oxidizer 418. The oxidizer 34 provides an output via a flow line 420 to the ion source. FIG. 4B illustrates an expanded view of the transfer capillary exit and the oxidizing reactor entrance.

Figure 5:
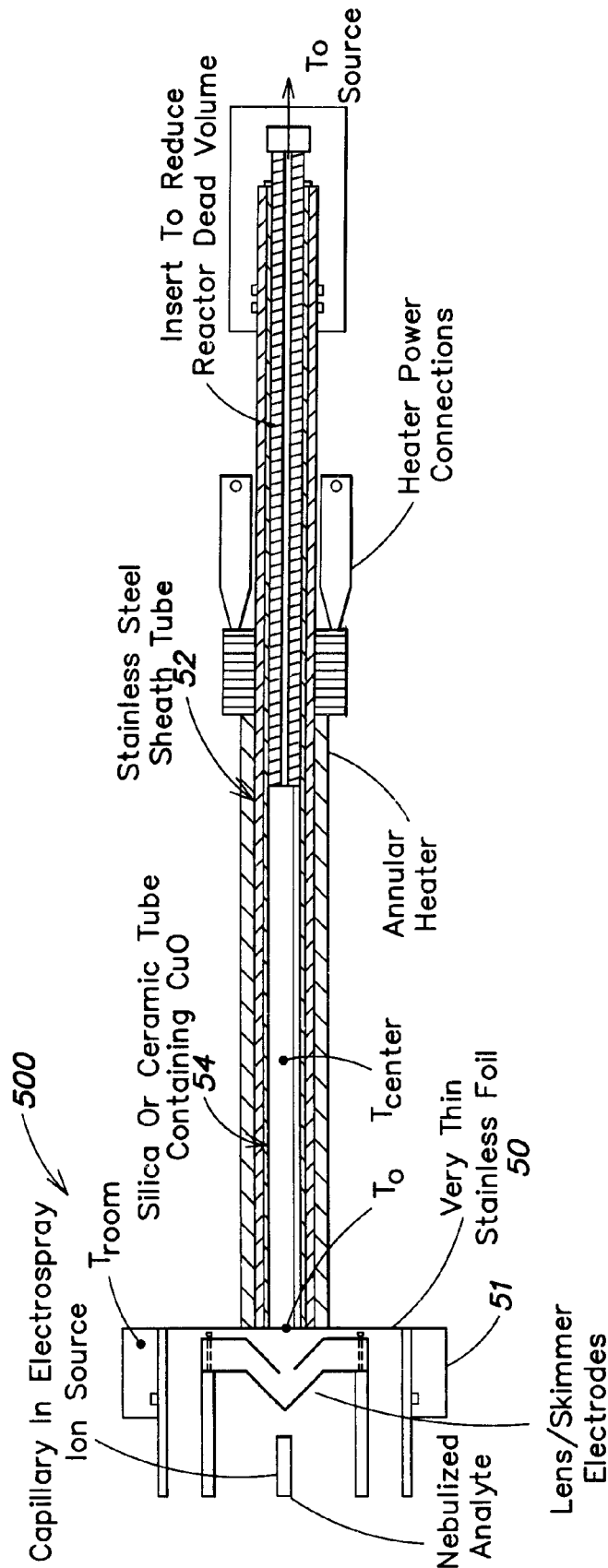
FIG. 5 illustrates a transfer capillary exit and oxidizing reactor embodiment.

The reactor tube may be heated to the required temperature by a number of techniques, including induction heating, resistive heating, radiative heating and convection heating. In a preferred embodiment, the furnace tube is placed in an annular (hollow) resistive heater with terminations on the output end (Type DS or DM heating element, L. J. Labaj, Inc., Niagara Falls, N.Y.). FIG. 5 illustrates a transfer capillary exit 500 and oxidizing reactor embodiment, illustrating a thin stainless foil connection 50 between adapter flange 51 and sheath tube 52. This results in a temperature profile in the furnace that rapidly increases to the maximum temperature, thus reducing the probability that analyte will be trapped in a low temperature region at the furnace entrance. A ceramic or fused silica reactor tube 54 is filled with CuO and inserted into the stainless steel sheath 52. The sheath is welded to the thin stainless foil, which is welded to an adapter flange, which establishes a vacuum seal with the electrospray ion source. The adapter flange is maintained at or near room temperature. If the stainless sheath has a relatively thick wall (~⅛ in.), and the stainless foil is very thin (~0.005 in.), most of the temperature drop between the reactor maximum temperature ($T_{center}$~750 deg. C.) and the adapter flange ($T_{room}$~25 deg. C.) will occur across the thin foil. Therefore, the temperature at the entrance to the furnace tube ($T_o$) will be close to the maximum temperature $T_{center}$. Ensuring that the temperature at the furnace entrance rapidly increases to the optimal value reduces the probability that analyte will be trapped in the furnace entrance in a region with a temperature too low to promote total conversion.

In this embodiment a primary function of the nebulizer 32 is solvent removal prior to oxidation. Solvent removal is important in the LC-AMS interface for several reasons including: (1) counts due to naturally occurring $^{14}$C in the solvent create a statistical noise background that limits the detection sensitivity for sample $^{14}$C, (2) excessive solvent in the analyte stream may result in $^{14}$C count rates which exceed the maximum detector count rate capability, (3) excessive solvent carbon entering the AMS ion source may exceed the C$^-$ current limit of the source, and (4) excessive carbon flow into the oxidizing reactor may result in oxygen depletion and reduction in analyte oxidation efficiency. Of these, factors (1) and (3) are the most restrictive. For example, for $^{14}$C detection, considering counting statistics only, in order to detect one amole of $^{14}$C with a signal-to-noise-ratio of 20, the $^{12}$C-flow rate from solvent must be below 30 nmoles/sec. For acetonitrile solvent, for example, this corresponds to a maximum solvent flow rate of 0.035 μL/min. A further restriction on solvent flow is imposed by the AMS ion source. Maximum C$^-$ ion currents from gas-fed AMS ion sources developed by other researchers are in the range 15–30 μA (see for example the article by C. R. Bronk and R. E. M. Hedges, Nucl. Instr. Meth. Phys. Res. B29 (1987) 45; also R. Middleton, J. Klein and D. Fink, Nucl. Instr. Meth. Phys. Res. B43 (1989) 231, both incorporated by reference). Using the low end of this range, and a negative ion production efficiency of 7%, the corresponding maximum carbon flow rate into the ion source is 2 nmoles/sec (0.0025 μL/min acetonitrile). Higher carbon flow rates from solvent can be handled by splitting the effluent stream from the oxidizer before it enters the AMS ion source. Since the quantity of $^{14}$C from analyte entering the ion source will also be reduced, the system sensitivity will be affected.

The transfer efficiency of analyte molecules through the electrospray nebulizer into the conversion reactor may be increased by adding sub-micron sized particles ("nanoparticles") to the sample stream before it enters the electrospray nozzle. These fine particles provide a nucleation site for the analyte molecules during the droplet evaporation process. The high mass (and corresponding high momentum) nanoparticles will enhance transfer efficiency of analyte molecules condensed thereon by decreasing the chance of deflection due to gas collisions. For applications which require desolvation (such as AMS detection of $^{14}C$), the gas stream typically passes through a number of elements such as capillary tubes, gas skimmers, and electrostatic lens electrodes. In this case, using a nanoparticle carrier should significantly enhance analyte transfer efficiency. Suitable inorganic nanoparticles are commercially available in silicon dioxide (available in sizes from 10 to 25 nm diameter from Nissan Chemical America Corp., Tarrytown, N.Y.) and cobalt (70 nm diameter from Vacuum Metallurgical Co., Ltd., Tokyo, Japan.) Additionally, there are a variety of other inorganic nanoparticles described in the scientific literature, for example, barium hexaaluminate (BHA). BHA is a combustion catalyst which can serve a dual role of carrier and catalyst, see for example "Reverse Microemulsion Synthesis of Nanostructured Complex Oxides for Catalytic Combustion", by A. J. Zarur and J. Y. Ying, Nature, vol 413, pp. 65–67, 2000, incorporated herein by reference.

FIG. 6A illustrates an alternative embodiment, wherein, a high temperature (~1450 deg. C.) reactor 600 (pyrolyzer) is used to convert sample hydrogen to $H_2$. This type of reactor has been shown to provide quantitative conversion of sample hydrogen to $H_2$ for organic compounds analyzed by GC-IRMS. See for example the paper by T. W. Burgoyne and J. M. Hayes, *Anal. Chem.* 70 (1998) 5136; H. J. Tobias and J. T. Brenna, *Anal. Chem.* 69 (1997) 3148; I. S. Begley and C. M. Scrimgeour, *Anal. Chem.* 69 (1997) 1530, incorporated herein by reference. The elimination of the desolvation requirement for tritium detection has important consequences in the design of a liquid sample introduction interface for AMS. First, the interface can be made simpler and more robust by elimination of the requirement for analyte/sample matrix separation (e.g., solvent removal) upstream of the AMS ion source. Accurate and facile calibration follows for a system that accepts an unfractionated flow as the technique of sample introduction. The ratio of counts at the high energy detector ($^3H$) to the current at the low energy Faraday cups ($^1H$ or $^2H$) translates directly into concentration once the ratio has been determined for reference standards. A sample introduction interface that removes solvent upstream from the ion source loses this straightforward technique for determining analyte concentration. Second, the volumetric flows are of the order to permit the application of microfluidic technologies to sample manipulations. These technologies lead to greatly increased sample throughputs largely as a result of decreased reaction and analysis times associated with microscaling.

This embodiment includes a camera 602 positioned with respect to a viewport 604 to facilitate the mechanical alignment of the contents of chamber 606. Sample is introduced to the chamber 606 via a flow line 608. The chamber 606 also receives He gas (e.g., 1 psig) via port 610, and includes a vent 612.

FIG. 6B is an exploded view of the connection between chamber 606 and reactor 600 of the embodiment illustrated in FIG. 6A. The chamber 606 includes a capillary 652 (e.g., 2 microns i.d.) that is operably positioned with respect to counter electrode 654 and alumina tube 656 (e.g., 5 mm i.d.). The reactor 600 also includes a heater 658.

Referring still to FIGS. 6A and 6B, in this embodiment all of the electrospray effluent can be directed into the pyrolysis furnace, obviating the need for an additional pumping chamber containing lens and skimmer electrodes, in contrast to the embodiment in FIGS. 4A–4B. As set forth above, desolvation is not a design objective in this embodiment. Nevertheless, electrospray is an efficient technique to promote nebulization of very low flows. The electrospray nebulizer includes the capillary 652 with provision for applying voltages to promote nebulization. Glass, quartz, and fused silica capillaries suitable for the purpose are commercially available. These capillaries 652 were developed for electrospray ionization for mass spectrometry and are available with inner diameters at the tip from 2 $\mu$m to 30 $\mu$m (New Objective, Inc, Cambridge, Mass.). The smallest have been used at flows as low as 1 nL/min. The capillary will be contained within a closed chamber that communicates with the pyrolysis chamber and has a pass-through for the capillary feed as well as a gas inlet and vent. There is also an alternative to capillaries. Glass microchips having channel openings at their edge will electrospray similar to a capillary. See for example the papers by Q. Xue, F. Foret, Y. M. Dunayevskiy, N. E. McGruer, and B. I. Karger, *Anal. Chem.* 69 (1997) 426; D. Figeys, Y. Ning, and R. Aebersold, *Anal. Chem.* 69 (1997) 3153; and N. Xu, Y. Lin, S. E. Hofstadler, D. Matson, C. J. Call, and R. D. Smith, *Anal. Chem.* 70 (1998) 3553, each incorporated herein by reference. The entire nebulized flow will be introduced directly into a pyrolysis chamber swept with carrier gas. At elevated temperatures, organic H is converted to $H_2$, even in the absence of a catalyst. The reaction pathway is quite complex and depends on many factors, but when there is an excess of elemental carbon available, the equilibrium-controlled fate of hydrogen is to become $H_2$. This fact has been exploited recently to design systems for on-line determination of hydrogen and oxygen isotope ratios in water and in organic compounds that can be analyzed by gas chromatography. See for example the paper by T. W. Burgoyne and J. M. Hayes, *Anal. Chem.* 70 (1998) 5136; H. J. Tobias and J. T. Brenna, *Anal. Chem.* 69 (1997) 3148; I. S. Begley and C. M. Scrimgeour, *Anal. Chem.* 69 (1997) 1530, incorporated herein by reference. The designs are conceptually simple, employing little more than an internal carbon coated alumina tube contained within a resistively heated furnace and connected to the inlet and outlet streams with conventional compression fittings. Hollow resistive tube heaters capable of operating at temperatures up to 1500 deg. C. are commercially available at low cost (L. J. Labaj, Inc., Niagara Falls, N.Y.). It has been reported that pyrolytic decomposition of organic compounds to $H_2$ is essentially quantitative when the pyrolyzer has been conditioned by deposition of a layer of carbon on the inner surface. For example see the paper by T. W. Burgoyne and J. M. Hayes, *Anal. Chem.* 70 (1998) 5136; H. J. Tobias and J. T. Brenna, *Anal. Chem.* 69 (1997) 3148; I. S. Begley and C. M. Scrimgeour, *Anal. Chem.* 69 (1997) 1530, incorporated herein by reference. Introduction of a mobile phase containing substantial amounts of water will consume carbon via the reaction $C+H_2H_2 \rightarrow H_2+CO$. Thus, it will be necessary to make provisions for sustaining the carbon layer in the pyrolyzer. It is contemplated that periodic introduction of carbon via the mobile phase and via the gas supply may be employed. One or more traps may be required to remove pyrolysis products other than $H_2$. Coupling the high temperature reactor to the electrospray chamber in the manner shown in FIG. 5 will help maintain a high temperature at the pyrolyzer input, and thus reduce condensation of analyte in a region where the temperature is too low to promote pyrolysis.

An alternate approach for directing the eluant from an LC or other device into a conversion reactor is to inject directly using a pipetter. Electrospray produces a cone of nebulized particles that diverge in space, thus limiting the amount of analyte that can be transferred into the conversion reactor. An alternative approach is to use a pipetter as the injection device. Any pipetter can be used, however, a piezo-electric pipetter offers certain advantages. A piezoelectric pipetter has the advantage that high velocity droplets of liquid are ejected that can travel distances of up to 30 cm in air. For the commercially available PicoPipette system (Engineering Arts, Mercer Island, Wash.), drops can be dispensed at a controllable rate up to at least 50,000 drops per second. Drop volume is typically 100 picoliters, with a typical drop diameter of 60 microns. This device incorporates a cylindrical piezo-ceramic element which surrounds a glass capillary with an inlet at one end and a nozzle at the other end. Compression of the piezo-ceramic element results in expulsion of a single droplet from the nozzle. Using a system of this type to inject liquid sample into a conversion reactor will result in extremely high analyte transfer efficiency for applications where separation of analyte from the mobile phase is not required, such as tritium analysis with AMS or C-14 analysis of samples where the mobile phase contains little or no carbon.

Figure 6A:
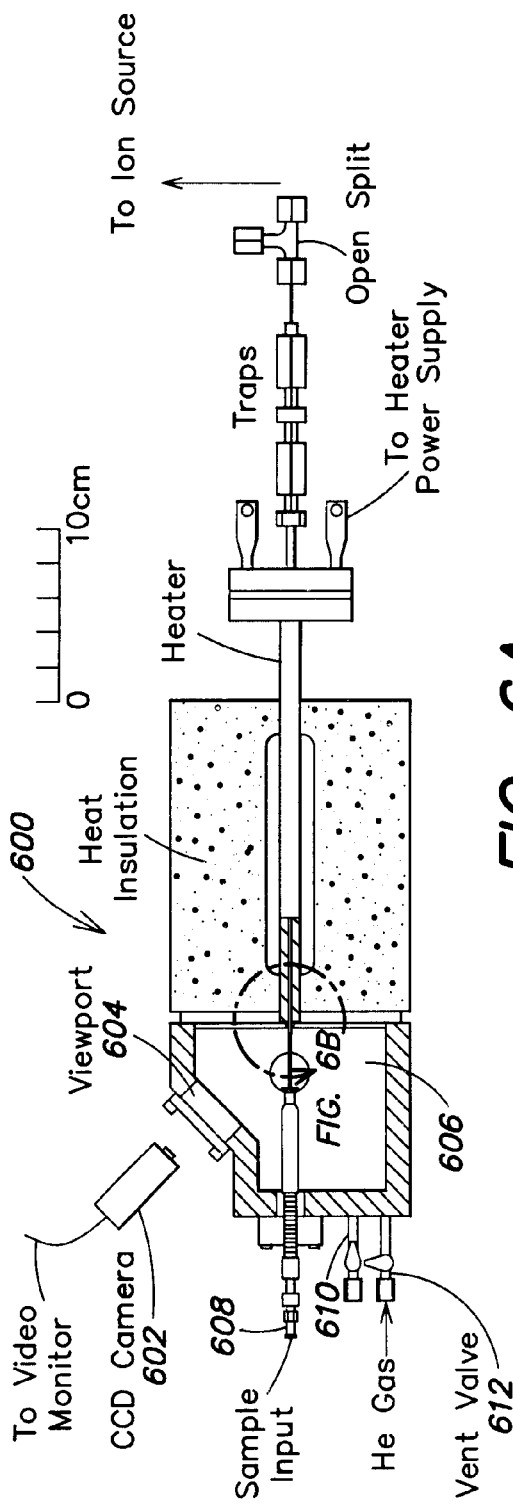
FIG. 6A illustrates an alternative embodiment, wherein, a high temperature (1450° C.) reactor (pyrolyzer) is used to convert sample hydrogen to $H_2$.
Figure 6B:
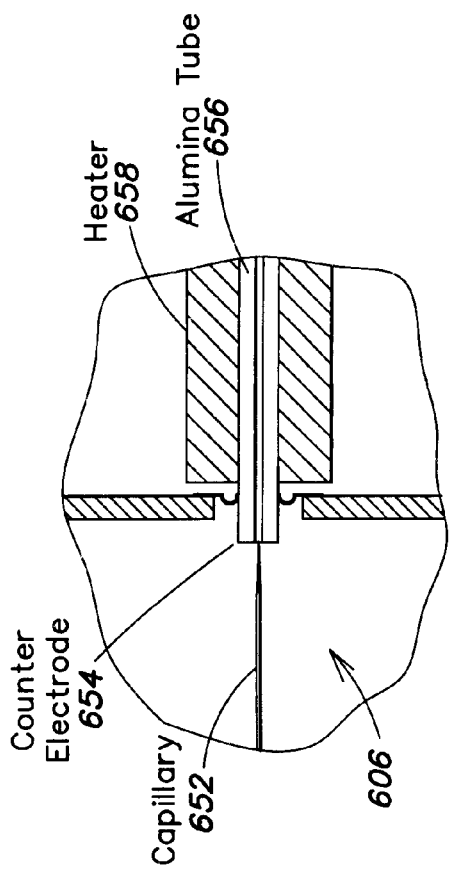
FIG. 6B illustrates an expanded view of an interface of the embodiment illustrated in FIG. 6A.

In another embodiment of the present invention, coupling of a microfluidic device to the AMS system is made possible by recent developments in coupling microfluidic devices to mass spectrometers using electrospray ionization. While the devices reported thus far are quite simple, they address several critical feasibility issues. It has been demonstrated, for example, that solutions can be electrosprayed from the opening of a microchannel at the edge of a chip, making possible sequential sampling of parallel channels. Flow switching between channels etched on a chip that are convergent to a single electrospray point is another embodiment. Sample purification by countercurrent dialysis on a chip that also electrosprays sample has been performed. See for example papers by Q. Xue, F. Foret, Y. M. Dunayevskiy, N. E. McGruer, and B. I. Karger, *Anal. Chem.* 69 (1997) 426; D. Figeys, Y. Ning, and R. Aebersold, *Anal. Chem.* 69 (1997) 3153; and N. Xu, Y. Lin, S. E. Hofstadler, D. Matson, C. J. Call, and R. D. Smith, *Anal. Chem.* 70 (1998) 3553, each incorporated herein by reference. The electrospray jet can be directed into a CuO reactor or high temperature pyrolyzer similar to those shown in FIGS. 4–6 for the required conversion of sample carbon to $CO_2$ (or hydrogen to $H_2$).

Figure 7:
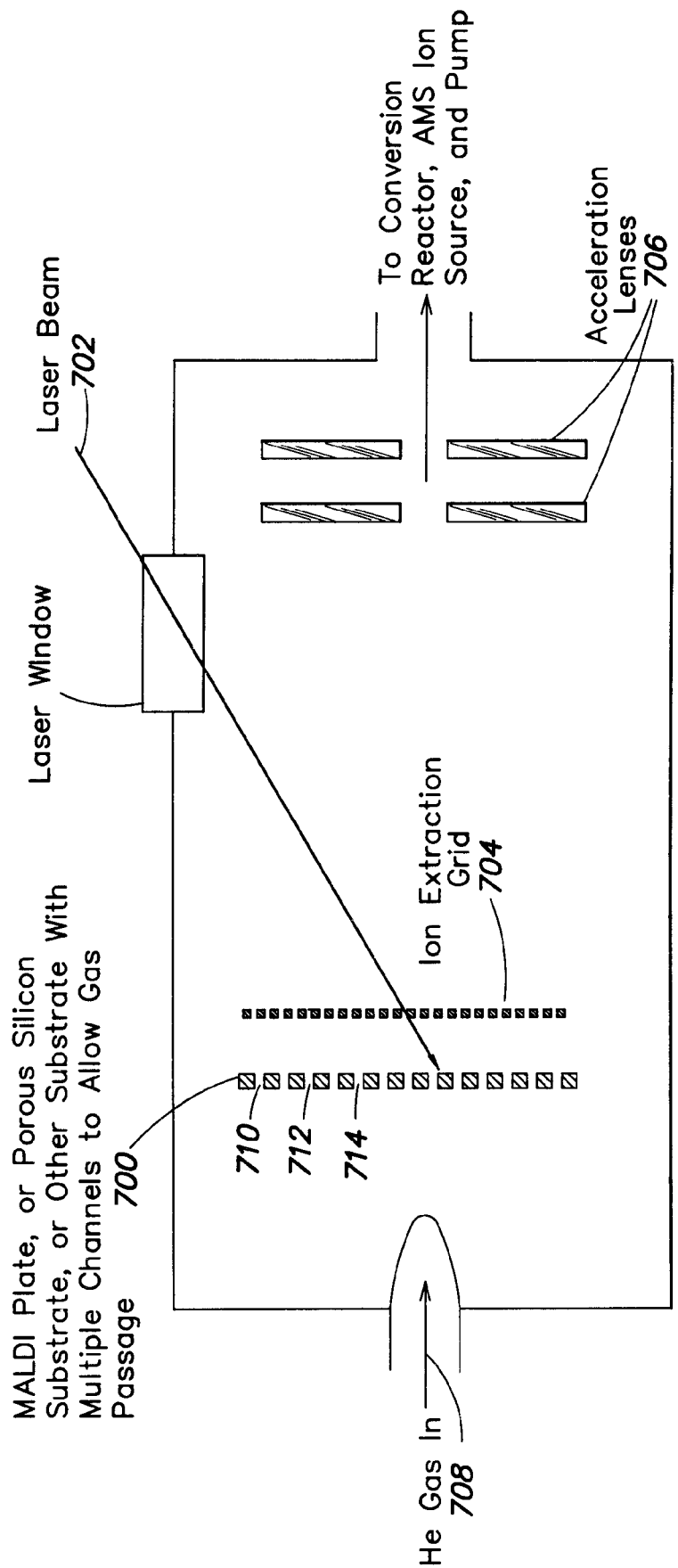
FIGS. 7 and 8A–8D illustrate a fourth embodiment of the present invention, coupling of laser-assisted desorption/ionization to a converter and then to the AMS.
Figure 8A:
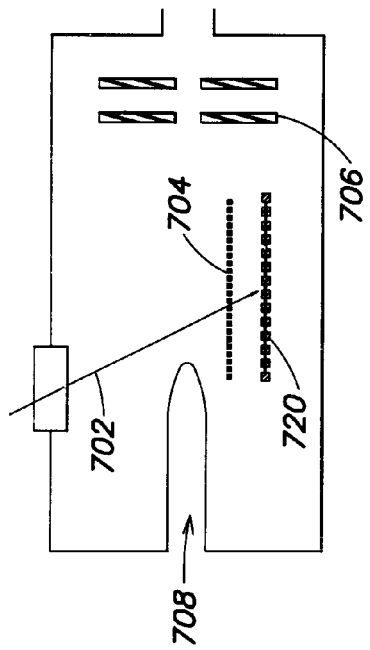
Figure 8B:
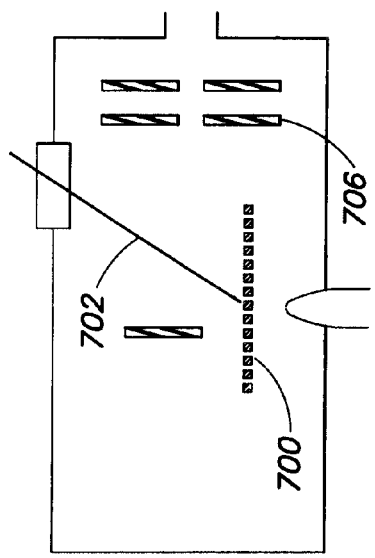
Figure 8C:
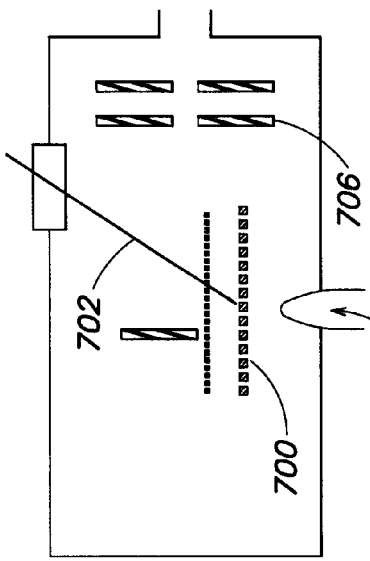
Figure 8D:
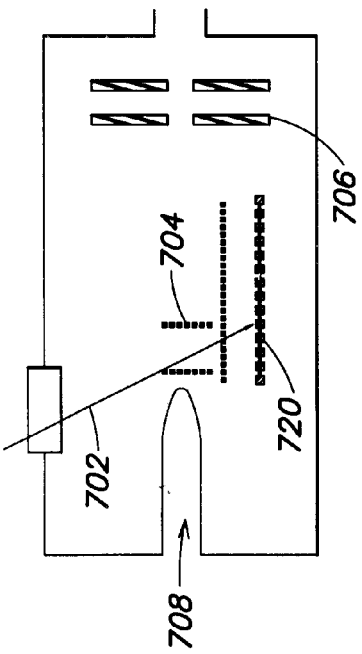

FIGS. 7 and 8A–8D illustrate a fourth embodiment of the present invention, coupling of laser-assisted desorption/ionization to the AMS. Laser desorption is used to nebulize analyte deposited on a suitable substrate. A substrate 700 is mechanically scanned through a fixed laser beam 702. The analyte molecules are not required to be ionized following desorption for this application; however, ionization is advantageous since electric fields can then be used to transport the molecules away from the surface and guide them to the conversion reactor entrance. Ion transport can be accomplished with one or more electrodes, as shown in FIG. 7. A first electrode is configured as a grid 704, and the subsequent electrodes comprise plates 706 with apertures to allow gas flow and ion transport. Carrier gas 708 must be introduced into the system upstream of the reactor to transport the reaction products to the AMS ion source. Referring still to FIG. 7, the carrier gas 708 is introduced via multiple channels (e.g., 710, 712, 714) in the substrate plate 700. Helium is shown, but other gases can be used. High molecular weight inert gases, such as argon or xenon, will increase momentum transfer to the analyte and may help move the analyte away from the surface after desorption, thus decreasing the probability of readsorption. Producing a high velocity jet may be advantageous to increase the momentum transfer from the carrier gas to the analyte molecules. Orientation of the electric field and carrier gas flow pattern will ensure high transmission efficiency of analyte to the conversion reactor. Other configurations for this embodiment are shown schematically in FIGS. 8A–8D. For the configurations illustrated in FIGS. 8B and 8C, the substrate plate is not required to allow gas passage, and thus a standard MALDI plate 720 may be used.

Since large, non-volatile molecules may be easily trapped, even on heated surfaces, the reactor design for the AMS interface must ensure efficient transfer of analyte molecules from the nebulization region to the conversion reactor. This is less important with the more volatile compounds analyzed with GC-AMS. Ion transport through the reactor entrance can be enhanced by applying an accelerating electric field with a pair of ring electrodes located at the reactor entrance and at some distance inside the reactor tube (for $CO_2$ production, the second ring electrode could be located immediately preceding the copper oxide).

Figure 9A:
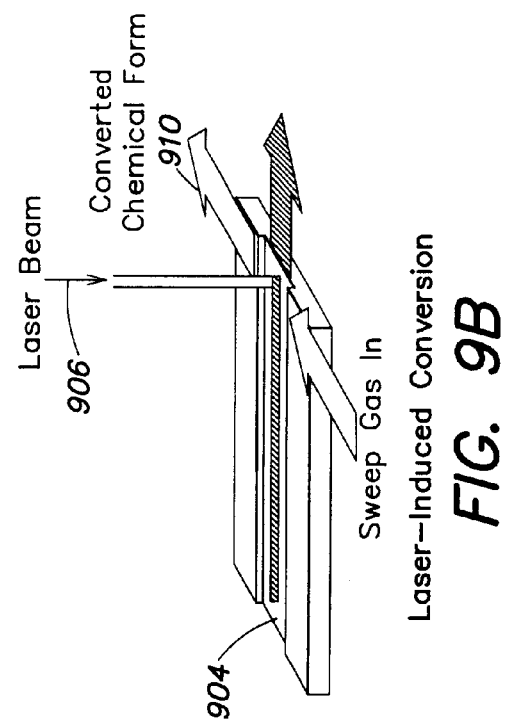
FIGS. 9A–9B illustrates a fifth embodiment of the invention, the laser-induced sample conversion method.
Figure 9B:
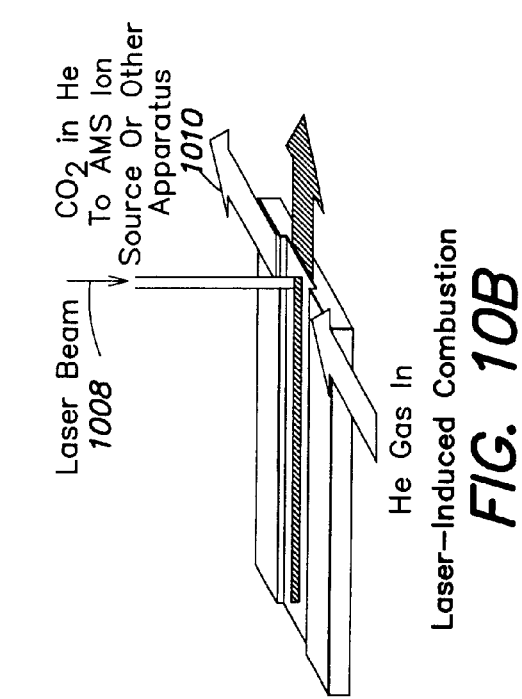

A fifth embodiment of the invention is illustrated in FIGS. 9A and 9B. Liquid or solid sample 902 is applied to a predefined region 904 on the surface of a substrate 900. The substrate 900 is then translated relative to a laser beam 906 in such a way that the laser beam deposits sufficient energy in the sample-containing region 904 on the substrate 900 to induce a chemical reaction(s) that converts constituents of the sample to the desired chemical form(s) 910. A sweep gas carries the converted chemical forms away from the reaction region and into an AMS or other apparatus (not shown). This embodiment is extremely versatile, and can be used with HPLC effluent or non-fractionated samples such as tissue homogenate. When used with HPLC, continuous analysis of a chromatogram is possible. When used with discrete (non-fractionated) samples, high sample throughput can be achieved with excellent sample-to-sample isolation. Preliminary experiments indicated that sample conversion efficiencies close to 100% can be obtained.

Figure 10A:
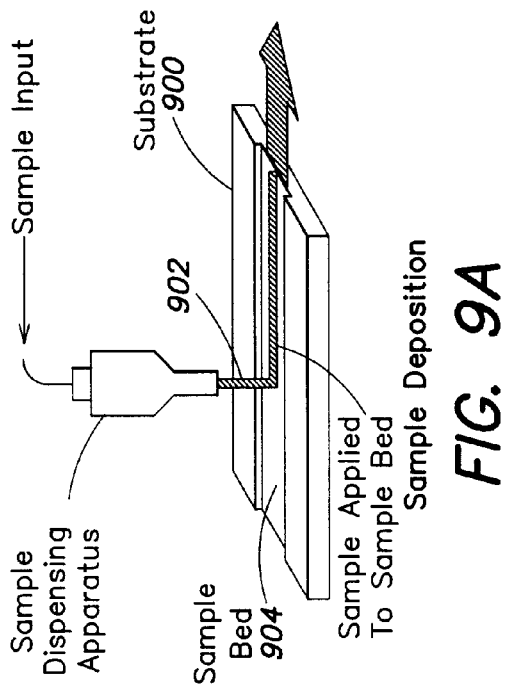
FIGS. 10A–10B illustrate the laser-induced sample conversion method for conversion of organic samples to $CO_2$ for AMS analysis or other applications.
Figure 10B:
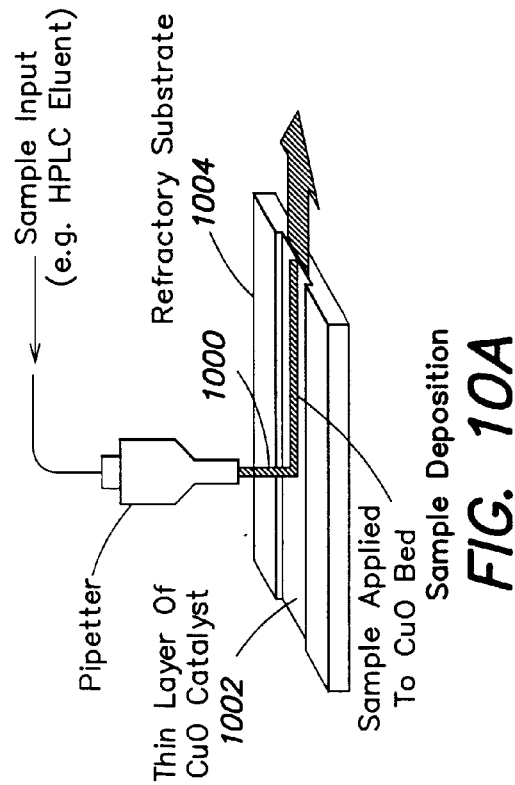

FIGS. 10A and 10B illustrate the application of the laser-induced sample conversion technique to the conversion of sample carbon to $CO_2$. The carbon-containing sample 1000 is first applied to a surface of a specially prepared catalyst bed 1002 on a refractory substrate 1004. Any volatile components of the sample, such as solvent present in HPLC eluent, are removed by evaporation. The catalyst bed 1002 is then translated through a reaction region where it is irradiated by a laser beam 1008. Local heating of the catalyst bed by the laser beam induces combustion of sample carbon to $CO_2$ 1010. Use of a low thermal conductivity, refractory substrate reduces cross-contamination caused by heating of adjacent samples. A constant flow of inert gas, such as He, removes the $CO_2$ directly from the site of formation and transports it to the AMS ion source.

An example of a suitable catalyst for conversion of organic or inorganic carbon-containing samples to $CO_2$ is copper oxide (CuO). Catalyst beds 1002 may be prepared by packing powdered CuO into a groove machined into one face of a refractory substrate, such as pure alumina or alumina fiber board. An alternative to packing CuO powder is to produce CuO in situ by pyrolytic decomposition of $CuNO_3$. This alternative is attractive because $CuNO_3$ is soluble in $H_2O$, so it can be applied to a variety of substrates by evaporation from solution. Solutions can not only be applied uniformly, but the concentrations can also be adjusted to yield precise amounts of $CuNO_3$ upon evaporation. As alternatives to CuO, other catalysts such as NiO, $PtO_2$, $V_2O_5$, may also be suitable for production of $CO_2$.

Fluid sample can be applied to the catalyst bed either in batch or continuous mode. In batch mode, each sample is applied to a discrete region of the catalyst bed that is well separated from other samples. Sample application may be accomplished using a pipetter, syringe, liquid dropper, or any other apparatus designed to dispense liquid. In continuous mode, the sample volume is distributed over a region of the catalyst bed in such a way that the spatial coordinates within the sample region bear a unique relationship to the time history of the sample flow. For example, this mode of sample application may be used to apply eluent from a liquid chromatography column to the catalyst bed in such a way that the distance along the distribution path corresponds to the time elapsed from the beginning of chromatographic analysis. Therefore, the spatial coordinates within the sample region bear a unique relationship to the time history of the sample flow. Desired elements present in the sample can then be converted to a predetermined gaseous form in such a manner that the time history of the evolved gas has a defined relationship to the spatial coordinates within the sample region, and the predetermined gaseous form is delivered to an accelerator mass spectrometer in a manner to preserve the time history of the evolved gas.

It is contemplated that any apparatus designed to dispense liquid may be used to apply sample to the catalyst bed, but apparatus that allows precise control of sample flow rate may be desirable. Examples of liquid dispensing systems with precisely controllable flow rates are syringe pumps such as the Harvard Model 55-2226 (Harvard Apparatus, Inc.) or the PicoPipette system (Engineering Arts, Inc., Mercer Island, Wash.). The latter system ejects individual 60–500 pL droplets at rates of zero to 50,000 droplets per second, and can be used to control the rate of deposition of sample on the catalyst bed with extremely high precision.

Before application to the catalyst bed, fluid samples may be either in solution or suspension. A variety of different solvents and suspension media may be used, including water, methanol, isopropanol, acetonitrile, and others. When solvent or suspension medium removal is required prior to sample analysis, this may be accomplished by passive evaporation after the sample is applied to the catalyst bed, by evaporation under reduced pressure or in a stream of inert gas, or by evaporation assisted by heating of the catalyst bed.

Alternately, samples may be applied to the catalyst bed in solid form. For example, discrete samples such as tissue may be placed one by one onto a continuous catalyst bed, or placed individually in wells containing catalyst in a catalyst plate, or combined with catalyst and then placed in wells in the catalyst plate. Solid samples may also be applied to the catalyst plate in powdered form, either directly onto a catalyst bed or first combined with powdered or liquid catalyst and placed onto the surface of a plate not previously loaded with catalyst.

After application of sample to the catalyst plate and evaporation of solvent or suspension medium (if applicable), the catalyst plate 1002 is exposed to a laser radiation beam in such a way that the laser beam 1008 intercepts the surface of the catalyst bed 1002 at the location(s) at which sample has been applied. The laser beam may be continuous or pulsed, and may be converging, diverging or collimated at the position of the catalyst bed. The power density in the laser beam, in conjunction with the rate of translation of the catalyst bed, must be chosen so that the power deposited per unit volume (or per unit time) in the catalyst bed is sufficient to locally heat the catalyst to a high temperature to induce combustion of sample carbon to $CO_2$ and to effect release of the $CO_2$ thus produced from the catalyst bed. Suitable types of lasers include $CO_2$ lasers, Nd-Yag lasers, nitrogen lasers, or any other type of laser with sufficient power and power density to meet the above requirement.

In place of a laser beam, other techniques for heating the catalyst bed to induce combustion may be employed in this invention. Other radiation techniques include incoherent radiation such as radiation from a visible, infra-red or ultra violet light source, microwave or millimeter-wave radiation, radio frequency radiation, x-rays, or gamma ray radiation. In the case of long wavelength radiation (e.g., RF, microwaves or millimeter-waves), a resonant cavity or waveguide may be used to concentrate radiant energy in a small region of space. Alternately, a particle beam, such as an electron beam, proton beam, or other light or heavy ion beam, may be directed at the catalyst bed. Heating elements, such as resistive heaters in thermal contact with the catalyst plate, may be employed, or electrical current may be passed directly through selected regions of the catalyst plate to effect heating.

Upon release from the catalyst bed, the $CO_2$ is carried away from the reaction site in a flow of sweep gas that is then directed into the AMS ion source or other apparatus. In most cases an inert gas, such as He, will be preferred. In some cases, use of a reactive gas may be desired. For example, a sweep gas containing $O_2$ may be used to assist in combustion of sample on the catalyst bed.

Figure 11A:
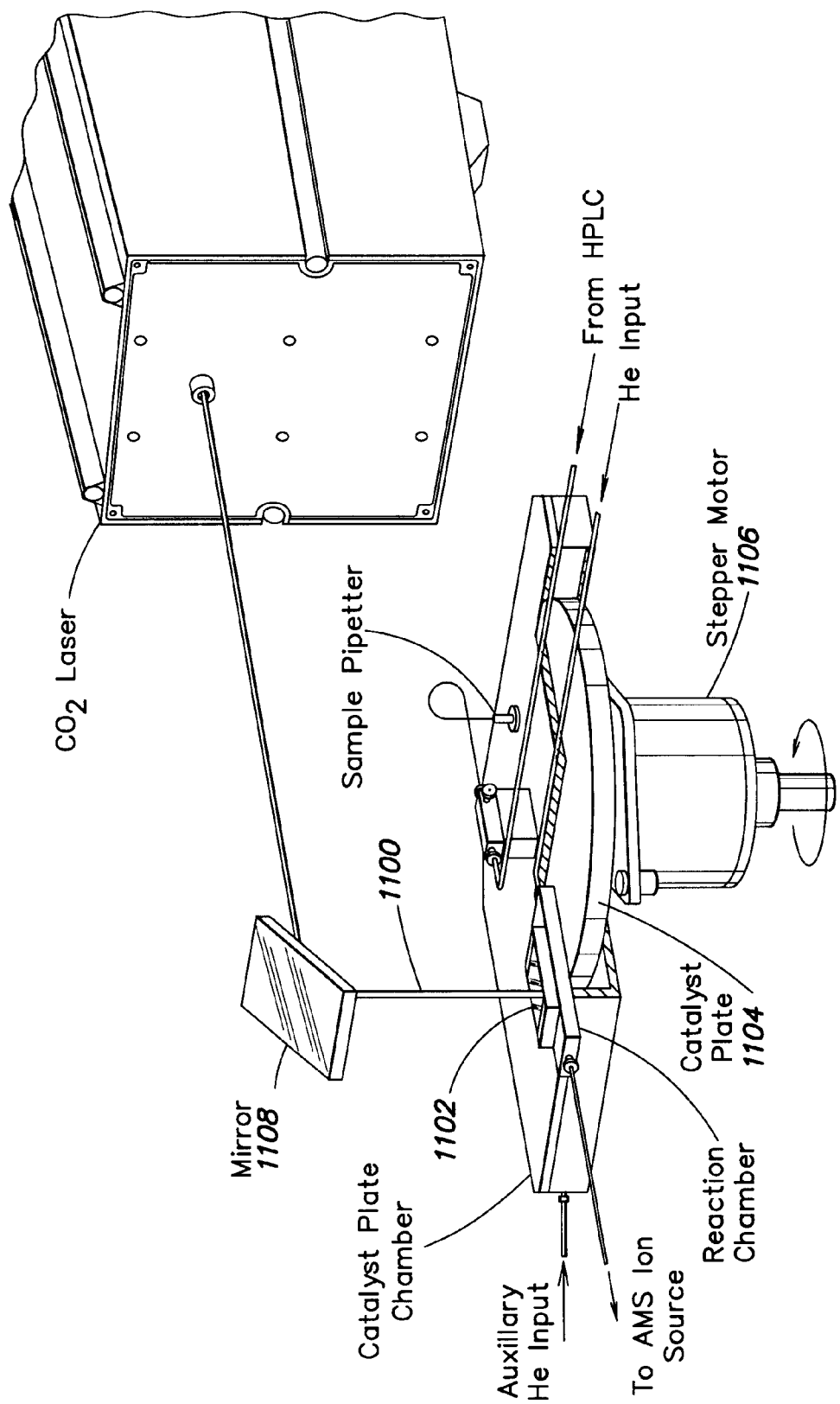
FIGS. 11A–11C illustrate an example of apparatus in which sample is moved past a fixed laser beam.

In order to irradiate different regions of a catalyst bed, either the bed can be translated past a fixed laser beam, or the laser beam can be directed to different regions of the bed, or both. An example of the first approach is shown schematically in FIG. 11A. In the figure, a laser beam 1100 is directed through a window 1102 in a sealed chamber containing the catalyst plate 1104. Any window material that is substantially transparent to the laser radiation may be used, such as a ZnSe window for $CO_2$ laser radiation. The catalyst plate 1104 is preferably disk shaped, and catalyst is applied to a circular region near the perimeter of the plate. In the simple embodiment shown, the laser beam 1100 is fixed and the catalyst plate 1104 is rotated using a motor 1106 to bring different regions of the circular catalyst bed into the laser beam 1100. If desired, access to any location of the catalyst plate may be obtained by scanning the laser beam 1100 in the radial dimension using a scanning device 1108 such as a moving mirror, in conjunction with rotation of the catalyst plate. In this case the transparent length of the window would be increased to cover the full radial extent of the catalyst bed. Yet another alternate approach would be one in which the catalyst plate 1104 was stationary and provisions were included for scanning the laser beam 1100 in either one or two dimensions. This may be accomplished, for example, using one or more moving mirrors.

Figure 11B:
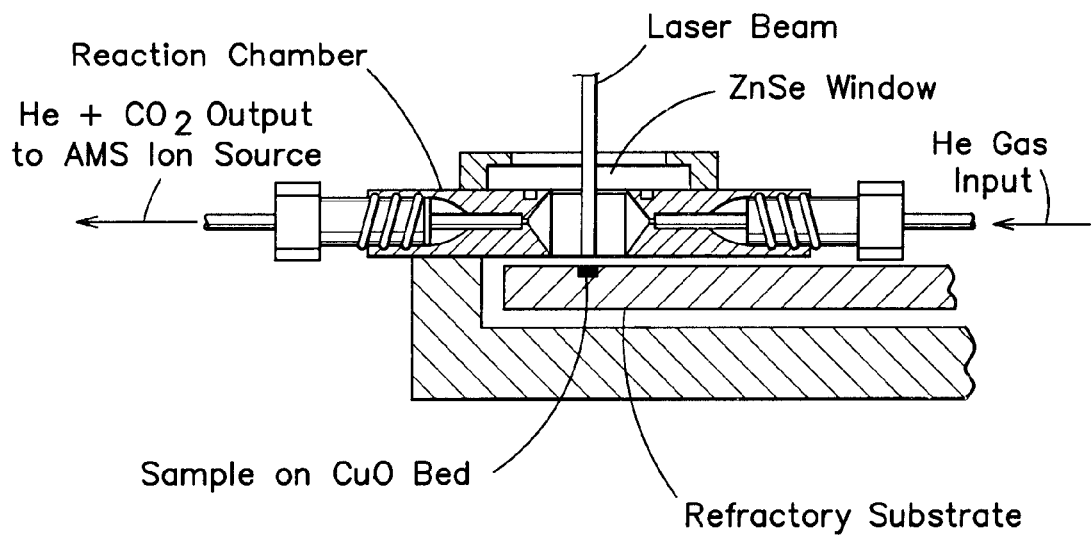
Figure 11C:
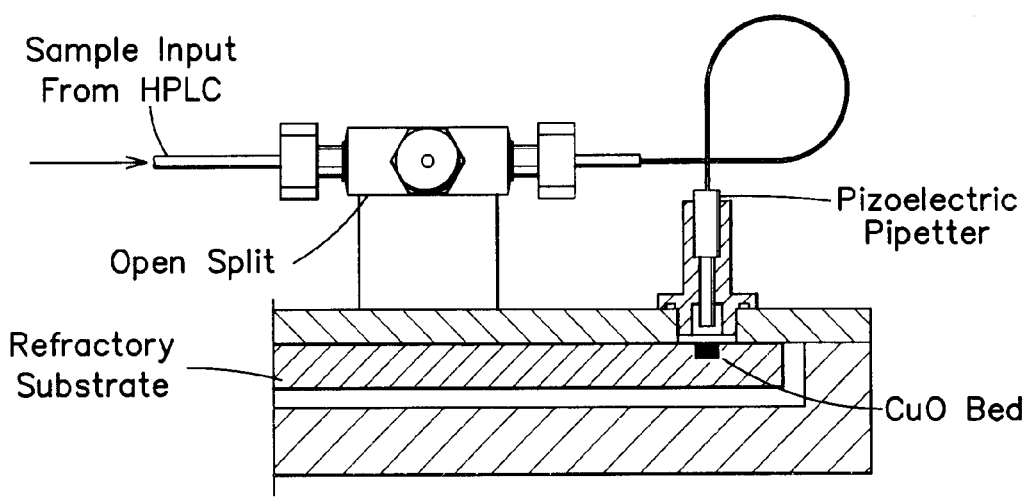

FIG. 11B is a cross sectional illustration of the reaction chamber and the catalyst plate chamber. FIG. 11C is a cross sectional illustration of the catalyst plate chamber in the region of the piezoelectric pipetter. The chamber containing the catalyst plate and reaction region can be operated at any pressure, but is preferably evacuated to reduce dead volume. A flow of gas sweeps reaction products from the chamber. The flow of sweep gas can be either continuous or pulsed. Any sweep gas flow rate can be used, but the flow rate is preferably compatible with the apparatus into which the reaction products are to be swept. For example, if the reaction products are swept into an AMS ion source, desirable flow rates will typically be in the range 0.1–10 ml/min.

The sweep gas may flow directly through the catalyst plate chamber, or the flow of sweep gas may be restricted to a smaller volume that communicates with the catalyst plate chamber only in the vicinity of the reaction region. Such a configuration is shown in FIG. 11B. It has the advantage that contact of the reaction products with surfaces of the catalyst plate, catalyst bed and reaction chamber is reduced, thereby reducing the probability of contamination of the reaction products with $CO_2$ from other sources, or contamination of other regions on the catalyst bed by the reaction products themselves.

In some cases, it is necessary to remove residual solvent from the catalyst bed. Because solvent and sample are applied together, combustion cannot be used to remove residual solvent. Instead, solvent can be rapidly removed by evaporation at elevated temperature. This has been demonstrated for LC-MS and LC-CRIMS interfaces developed by other researchers. See for example the papers by Caimi, R. J. and Brenna, J. T., *Anal. Chem* 65:3497-35—, 1993; Moini, M. and Abramson, F. P., *Biological Mass Spectrometry* 20:308–312, 1991; Brand, W. A. and Dobberstein, P., *Isotopes Environ. Health Stud.* 32:275–283, 1996; and U.S. Pat. No. 4,055,987, each incorporated herein by reference. Quantitative removal of solvent (methanol or water) from LC eluent applied to a moving wire or metal strip has been reported using a drying oven maintained at 150° C. Residence time in the drying oven was typically less than a second. Solvent removal of 99.999% has been reported for a Finnigan moving strip interface.

Figure 15:
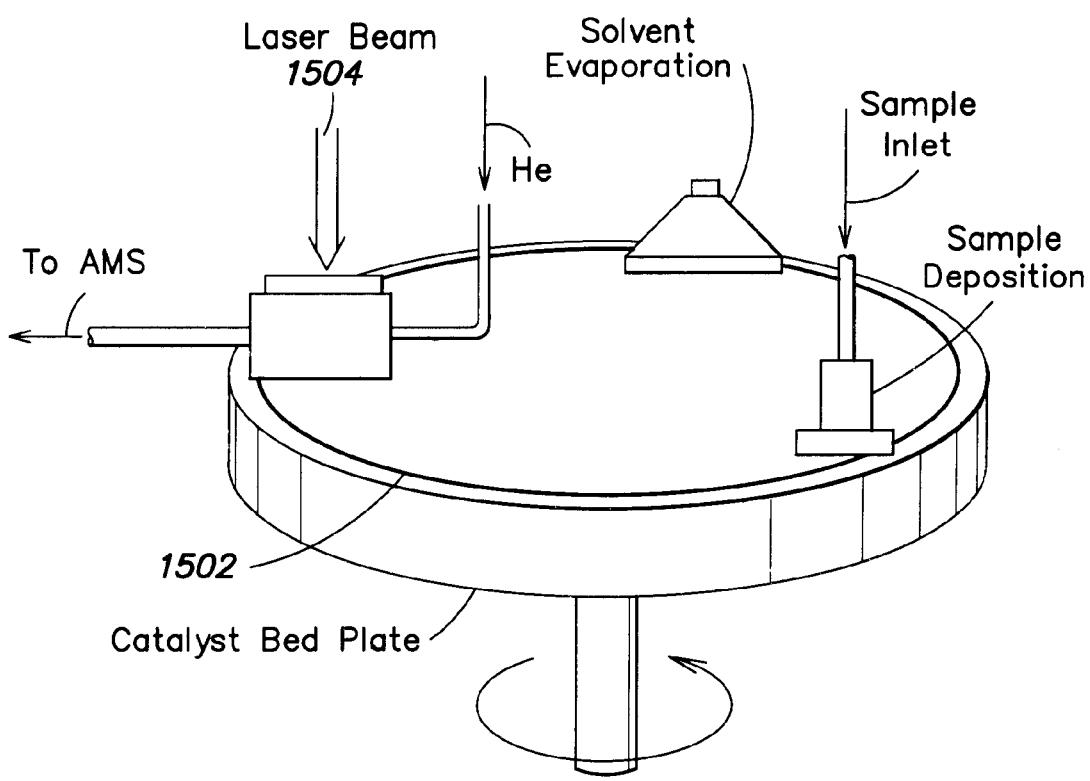
FIGS. 15 and 16 illustrate interfaces for continuous processing.
Figure 16:
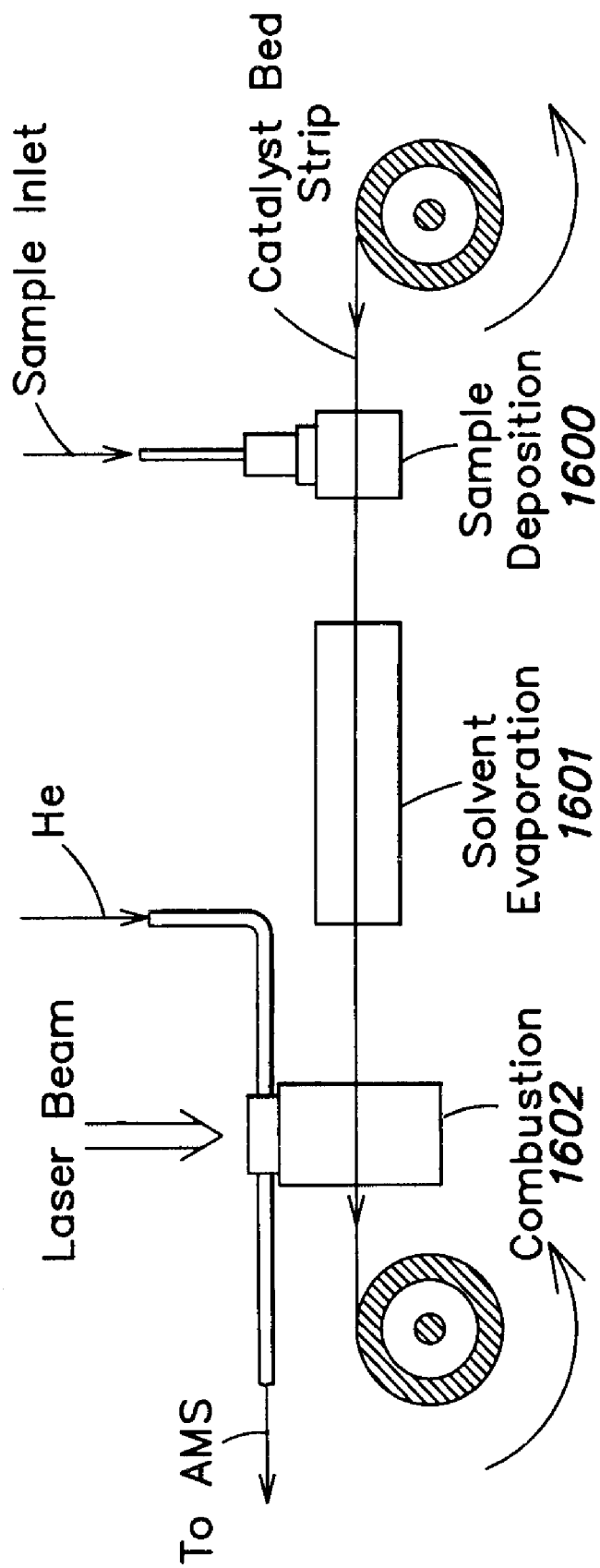

The laser-induced sample conversion technique can be used for both plate-by-plate and continuous processing. Two approaches to the design of a continuous interface are shown in FIGS. 15 and 16. A first approach is illustrated schematically in FIG. 15, and utilizes a rotating CuO-coated disk substrate 1502 on which a sample is deposited, heated to effect rapid solvent evaporation, and then rotated into the laser beam 1504 and combusted to $CO_2$. This approach has the advantages of mechanical simplicity and compactness, but may be better suited for plate-by-plate rather than continuous processing. In the simplest scenario, the steps of sample deposition, solvent evaporation and laser combustion take place sequentially, thus allowing volatilized solvent to be pumped from the chamber prior to laser combustion of sample. In a second approach, shown in FIG. 16, a moving strip substrate is used. The substrate is first coated with CuO using a powder deposition system, and then passes sequentially through a series of chambers 1600–1602 in which sample is applied, solvent is evaporated, and laser-induced combustion produces labeled $CO_2$ for AMS analysis, respectively. This approach can accommodate very long substrate lengths, facilitating the continuous analysis of HPLC eluent. It also provides the possibility for a high degree of isolation between the solvent evaporation and laser combustion stages, allowing these functions to be performed concurrently on different portions of the substrate. The moving strip approach (using a metal ribbon or wire) has been used successfully to couple HPLC and CRIMS, a situation that requires similar steps of sample deposition, solvent evaporation, and combustion to $CO_2$. See for example the papers by Caimi, R. J. and Brenna, J. T., *Anal. Chem* 65:3497-35—, 1993; and Moini, M. and Abramson, F. P., *Biological Mass Spectrometry* 20:308–312, 1991.

The laser-induced sample conversion technique can also be used for conversion of sample hydrogen to $H_2$ for AMS analysis, as illustrated in FIGS. 12A and 12B. Pyrolysis of organic compounds in the presence of excess elemental carbon results in the production of molecular hydrogen from the hydrogen atoms present in the compounds. The resultant molecular hydrogen is suitable for determination of hydrogen isotope composition by AMS. In this case, sample is applied to a bed of elemental carbon, instead of a catalyst bed, and $H_2$ is removed in the sweep gas. All other aspects of the method and apparatus discussed previously also apply to hydrogen conversion, with the substitution of carbon for oxidizing catalyst.

The laser-induced sample conversion method and apparatus may also be used in other applications requiring conversion of sample carbon to $CO_2$ or sample hydrogen to $H_2$. An example of such other applications is Isotope Ratio Mass Spectrometry (IRMS). In addition, the laser-induced sample conversion technique may be used to convert complex molecules into simple forms of other elements. For example, nitrogen oxides are produced under the same conditions of catalytic combustion used to produce $CO_2$. Carbon monoxide is also produced, and it may be used to determine oxygen isotope composition. The technique may also be used to convert complex organic matter in solution or suspension into simpler forms for AMS analysis or for introduction into other instruments. Examples of such complex matter include humic substances, sedimentary mixtures, geochemical deposits, fossils, microbes, and animal and plant tissues. Samples and chemical species useful in IRMS and other isotope monitoring techniques are described in publications: *Science* 236:543 (1987); *Ann. Rev. Nucl. Part. Sci.* 30:437 (1980); and J. Kielson and C. Waterhouse, *Proc. 1st Rochester Conference on Radiation Dating with Accelerators,* Univ. of Rochester, Rochester, N.Y. 391 (1978). Conversion of complex organic molecules in a waste stream into safer, less toxic forms is also possible using this invention. In such an application, any gaseous by-products of the chemical reactions that result in waste conversion would be removed from the reaction chamber and disposed of accordingly.

In all of the embodiments described above, excess $O_2$ as well as undesired oxides and hydrides may be trapped prior to the ion source using getters. It may be desirable to trap residual $O_2$, $NO_x$, and $H_2O$ before admitting the gas stream to the ion source to reduce the production of $O^-$, as well as $^{12}CH_2^-$ and $^{13}CH^-$. Removal of $H_2O$ will be advantageous to reduce production of the primary sources of background to $^{14}C$ measurements: $^{12}CH_2$, $^{13}CH$, and their fragments. Removal of water vapor from a helium gas stream containing $CO_2$ has been accomplished using a magnesium perchlorate trap. See for example the papers by J. C. Clark and L. P. D. Buckingham, entitled "Short-lived Radioactive Gases for Clinical Use" (Butterworths, Boston, 1975), p. 49; and R. E. M. Hedges, M. J. Humm, J. Foreman, G. J. Van Klinken and C. R. Bronk, *Radiocarbon* 34 (1992), 306, both incorporated by reference. Commercial traps for removal of $O_2$ and $H_2O$ from an inert gas stream are also available (e.g., Supelpure-O Trap, Supelco, Inc., Bellefonte, Pa.). In a preferred embodiment, the water removal trap is a Nafion gas dryer (Perma Pure, Inc. Toms River, N.J.). Nafion is a copolymer of perfluoro-3,6-dioxa-4-methyl-7-octene-sulfonic acid and tetrafluoroethylene (TEFLON®) which readily absorbs water by attachment to the sulfonic acid group. Nafion gas dryers are highly selective, and normally remove only water, ammonia, and alcohols. Nafion can be used even to remove water from a hydrogen gas stream.

In the second embodiment of this aspect of the invention, conversion of isotope in a sample into a chemical form suitable for AMS analysis is effected by introduction of sample on a suitable substrate into the AMS ion source and exposure of the sample to a localized form of energy within the ion source. This embodiment is illustrated in FIGS. 13A and 13B. As in the first embodiment described above, sample 1300 is applied to a substrate 1302 in either solid or liquid form using an appropriate dispensing apparatus 1304, and a sample-containing region 1306 on the substrate 1302 is then translated through a region within the ion source chamber in which the sample is exposed to a source of energy 1308. Conversion of sample elements to ionic species 1310 takes place through the action of the energy source on the sample.

Figure 14B:
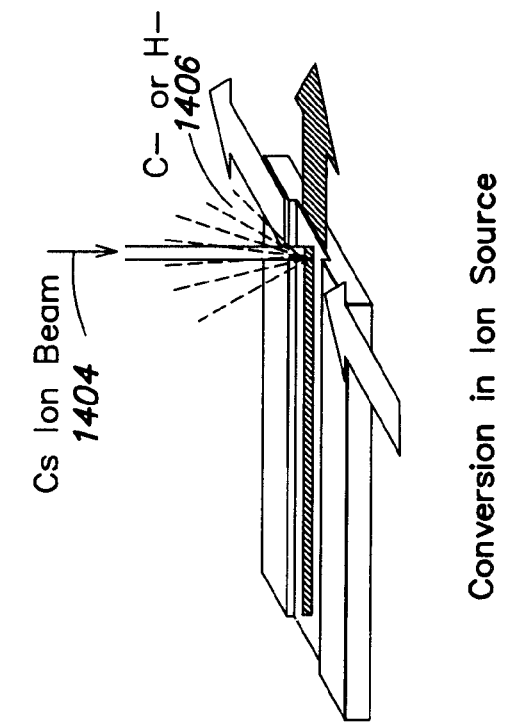
FIGS. 14A–14B illustrate sample conversion in the AMS ion source using a Cs ion beam.
Figure 14A:
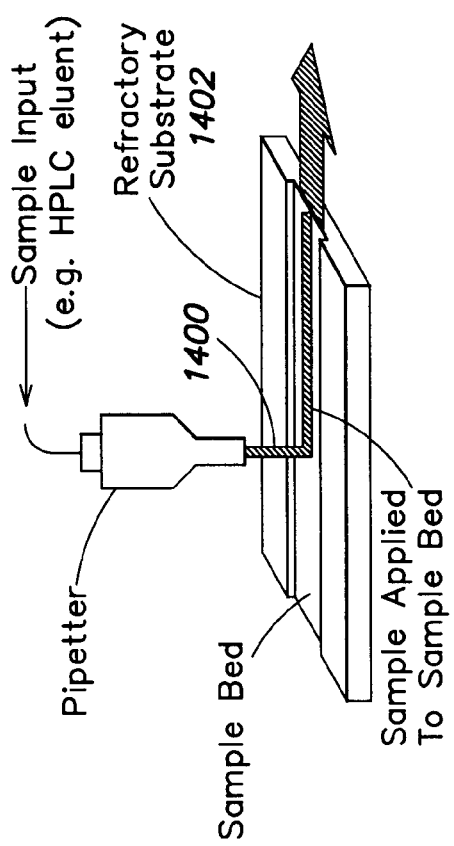

An example of the second embodiment of the invention is the conversion of carbon or hydrogen in complex samples into $C^-$ or $H^-$ in a cesium-sputter negative ion source, as illustrated in FIGS. 14A and 14B. Cesium sputter ion sources of this type are described in publications: *Nucl. Instr. and Method* B52:517 (1990); and *Nucl. Instrum. Meth. Phys. Res.* B92:445 (1994). Sample 1400 is applied to a surface of a substrate 1402 that is then moved through a focused Cs ion beam 1404 within the ion source chamber. In contrast to the conventional practice of converting the sample to solid graphite prior to introduction into the ion source chamber, the present invention introduces the sample in its native form, either as a solid or a liquid, in accordance with the techniques described above. That is, the step of dispensing sample onto the substrate is performed outside of the ion source chamber, and the substrate 1402 is then introduced into the ion source chamber and translated relative to the Cs beam 1404. This step facilitates the removal of solvent or suspension medium from the sample by evaporation, and distinguishes the present invention from other techniques in which chromatography effluent is applied directly to a surface within the ion source, as for example in publication *Nucl. Instrum. Meth. Phys. Res.* B92:445 (1994). Conversion of sample carbon or hydrogen to negative ions of $C^-$ or $H^-$ 1406 respectively takes place on the substrate surface under Cs beam bombardment. Conversion to negative ions on the substrate surface may be a single-step or a multi-step process, and may or may not require the presence of catalyst or other elemental or chemical forms. An example of a two-step process is one in which the first step is heating of the sample bed by the Cs beam to a sufficiently high temperature for chemical conversion of sample carbon or hydrogen to an intermediate chemical form, followed by production of negative ions from that chemical form in the presence of Cs.

Although the present invention has been shown and described with respect to several preferred embodiments thereof, various changes, omissions and additions to the form and detail thereof, may be made therein, without departing from the spirit and scope of the invention.

What is claimed is:

1. A method of converting a non-gaseous sample for accelerator mass spectrometry analysis, comprising:
   applying the sample to a solid substrate;
   transferring the substrate to an accelerator mass spectrometry ion source; and
   converting the desired elements present in the sample to the desired ionic species for accelerator mass spectrometry analysis.

2. The method of claim 1, wherein said step of converting comprises bombarding the sample with a cesium beam.

3. The method of claim 1, wherein after applying the sample to the solid substrate, the method comprises evaporating volatile components from the sample.

4. The method of claim 1, wherein said step of converting comprises converting carbon in the sample to negative carbon ions.

5. The method of claim 1, wherein said step of converting comprises converting hydrogen in the sample to negative hydrogen ions.

6. A method of converting a non-gaseous sample for accelerator mass spectrometry analysis, comprising:
   depositing the sample on a solid substrate;
   converting desired elements present in the sample to a predetermined gaseous form; and
   providing the predetermined gaseous form to an accelerator mass spectrometry ion source.

7. The method of claim 6, wherein after applying the sample to the solid substrate, the method comprises removing volatile components from the sample.

8. The method of claim 6, wherein said step of converting comprises converting carbon in the sample to carbon dioxide.

9. The method of claim 6, wherein said step of converting comprises converting hydrogen in the sample to molecular hydrogen.

10. The method of claim 6, wherein said step of converting comprises heating the sample with a localized energy source.

11. The method of claim 10, wherein said step of heating comprises irradiating the sample with a laser beam.

12. The method of claim 11, wherein said step of heating comprises translating the substrate relative to a laser beam in such a way that the laser beam deposits sufficient energy in a sample containing region on the substrate to induce a chemical reaction that converts constituents of the sample to the predetermined gaseous form.

13. The method of claim 6, wherein the substrate comprises a refractory material.

14. The method of claim 6, wherein the sample-containing region of the substrate comprises a catalyst.

15. The method of claim 14, wherein said catalyst comprises copper oxide.

16. The method of claim 6, wherein the sample-containing region of the substrate comprises elemental carbon.

17. A method of converting a non-gaseous sample for analytical processing, comprising:
   depositing the sample on a solid substrate;
   converting desired elements present in the sample to a predetermined gaseous form using a beam of directed energy; and
   providing the predetermined gaseous form to an analytical device for processing.

18. The method of claim 17, wherein said analytical device comprises an accelerator mass spectrometer.

19. The method of claim 17, wherein said analytical device comprises an isotope ratio mass spectrometer.

20. The method of claim 17, wherein the directed energy beam comprises a laser beam.

21. The method of claim 17, wherein the sample-containing region of the substrate comprises a copper oxide catalyst.

22. The method of claim 17, wherein the sample-containing region of the substrate comprises elemental carbon.

23. The method of claim 16 wherein th e sample comprises substantially unfractionated biological material such as blood, urine, or tissue homogenate.

24. A method of analyzing a liquid sample by accelerator mass spectrometry, comprising:
   distributing the liquid sample over a region of a substrate in such a manner that the-spatial coordinates of the location of the sample on the sample region bear a unique relationship to the time history of the flow of the sample onto the region;

converting desired elements present in the sample to a predetermined gaseous form in such a manner that the time history of the evolved gas has a defined relationship to the spatial coordinates within the sample region; and delivering the predetermined gaseous form to an accelerator mass spectrometer in a manner that preserves the time history or the evolved gas.

25. The method of claim 24, wherein prior to deposition on the substrate, at least a portion of the chemical constituents of said liquid sample are substantially separated by liquid chromatography.

26. The method of claim 24, wherein prior to deposition on the substrate, at least a portion of the chemical constituents of said liquid sample are substantially separated by capillary electrophoresis.

27. The method of claim 24 wherein said step of converting comprises irradiating the sample with a laser beam.

28. The method of claim 24 wherein volatile components of the liquid sample are removed prior to said step of converting.

29. The method of claim 24 wherein carbon in said sample is converted to carbon dioxide.

30. An interface system for introducing a non-gaseous sample as a predetermined gaseous form into an analytical instrument, said interface system comprising:

a substrate that receives the non-gaseous sample; and a directed energy source that heats at least a portion of said substrate containing the non-gaseous sample to convert the sample to the predetermined gaseous form.

31. The interface system of claim 30 wherein the directed energy source comprises a laser.

32. The interface system of claim 30, wherein at least a portion of the substrate that receives the non-gaseous sample comprises a catalyst.

33. The interface system of claim 32, wherein the catalyst material comprises copper oxide.

34. The interface system of claim 30, further comprising means for removing volatile portions of the non-gaseous sample prior to conversion to the predetermined gaseous form.

35. The interface system of claim 30, further comprising a chamber wherein the directed energy source heats at least a portion of said substrate, said chamber comprising an input port and output port configured and arranged to receive a carrier gas and provide the predetermined gaseous form in said carrier gas.

36. The interface of claim 35, wherein said carrier gas comprises He.

37. An interface system for detecting specific atoms in specific chemical constituents of a liquid sample with an accelerator mass spectrometer, said system comprising:

a liquid chromatograph for substantially separating the chemical constituents of the sample;

a liquid deposition system that receives the eluant of the liquid chromatograph and delivers it as a series of droplets or as a substantially continuous liquid stream;

a substrate onto which said series of droplets or liquid stream is spatially distributed in such a manner that the spatial coordinates of the sample location on the distributed sample region bear a defined relationship to the elution time of each chemical component from the liquid chromatograph;

a chamber in which a localized energy source converts the sample to a predetermined gaseous form in a manner so that the time history of the evolved gas bears a unique relationship to the spatial coordinates, and thus to the chromatographic elution time; and a flow line that transports the predetermined gaseous form to an accelerator mass spectrometer in a manner that preserves the time history.

38. The interface of claim 37, wherein said liquid deposition system is configured and arranged to provide a series of droplets or a substantially continuous liquid stream with diameter less than about 500 $\mu$m.

39. The interface of claim 38 wherein the liquid deposition system comprises a piezoelectric pipetter.

40. The interface of claim 37 wherein volatile components are removed prior to conversion of the sample to the predetermined gaseous form.

41. The interface of claim 37 wherein the localized energy source comprises a laser.

42. The interface of claim 41 wherein said laser comprises a carbon dioxide laser.

43. The interface of claim 37 wherein the sample-containing region of the substrate comprises copper oxide.

44. The interface of claim 37 wherein the liquid stream from the liquid deposition system is distributed in a substantially circular path on the substrate, wherein distance along the path bears a defined relationship to the chromatographic elution time.

45. The interface of claim 44, wherein the substrate is substantially disk-shaped and the sample distribution is accomplished by rotating the disk relative to a fixed liquid deposition system.

46. The interface of claim 37, wherein conversion of distributed sample eluted from the chromatograph during some time period occurs concurrently with deposition of sample eluted from the chromatograph during some later time period.

47. The interface of claim 37 wherein the substrate comprises a moving strip, and sample distribution is accomplished by translating the strip relative to a fixed liquid deposition system.

* * * * *